US012778546B2

(12) United States Patent
Jeong et al.

(10) Patent No.: US 12,778,546 B2
(45) Date of Patent: Nov. 3, 2026

(54) ULTRASONIC IMAGING APPARATUS

(71) Applicant: Samsung Medison Co., Ltd., Hongcheon-gun (KR)

(72) Inventors: Manho Jeong, Seoul (KR); Changhyeong Shin, Seoul (KR); Kuil Jang, Seoul (KR); Jungmin Kim, Seoul (KR); Sokjae Shin, Seoul (KR); Hyungwon Yoon, Seoul (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 287 days.

(21) Appl. No.: 18/621,937

(22) Filed: Mar. 29, 2024

(65) Prior Publication Data

US 2024/0341725 A1 Oct. 17, 2024

(30) Foreign Application Priority Data

Apr. 11, 2023 (KR) ........................ 10-2023-0047821
May 23, 2023 (KR) ........................ 10-2023-0066500

(51) Int. Cl.
*A61B 8/00* (2006.01)
*B25J 9/10* (2006.01)

(52) U.S. Cl.
CPC ............ *A61B 8/4218* (2013.01); *A61B 8/467* (2013.01); *B25J 9/1065* (2013.01)

(58) Field of Classification Search
CPC ....... A61B 8/4218; A61B 8/467; B25J 9/1065
See application file for complete search history.

(56) References Cited

U.S. PATENT DOCUMENTS

| | | | |
|---|---|---|---|
| 6,663,569 B1 | 12/2003 | Wilkins et al. | |
| 9,504,447 B2 | 11/2016 | Messina et al. | |
| 10,695,028 B2 | 6/2020 | Zhao et al. | |
| 10,723,012 B1 * | 7/2020 | Jordan | F16M 11/2014 |

(Continued)

FOREIGN PATENT DOCUMENTS

| | | |
|---|---|---|
| CN | 102160802 B | 8/2016 |
| CN | 110087552 A | 8/2019 |

(Continued)

OTHER PUBLICATIONS

Extended European Search Report dated Aug. 30, 2024 issued in European Patent Application No. 24165730.3.

(Continued)

*Primary Examiner* — Sean A Frith
(74) *Attorney, Agent, or Firm* — Morgan Lewis & Bockius LLP

(57) ABSTRACT

An ultrasonic imaging apparatus includes a main body, a connecting unit configured to rotate and move with respect to a first connection frame provided on the main body, and a control panel provided on an end of the connecting unit to be movable up, down, right, left, or diagonally while remaining horizontal with respect to the main body, wherein the connecting unit includes a first arm provided with four link bars forming a parallelogram in a same plane and configured to rotate and move with respect to the main body and a second arm provided with four link bars forming a parallelogram in a plane provided independently of the first arm and configured to rotate and move with respect to the first arm.

17 Claims, 45 Drawing Sheets

(56) References Cited

U.S. PATENT DOCUMENTS

| | | | | |
|---|---|---|---|---|
| 2010/0094130 | A1 | 4/2010 | Ninomiya et al. | |
| 2010/0204578 | A1* | 8/2010 | Schmidt | A61B 8/4281 600/443 |
| 2011/0201927 | A1 | 8/2011 | Hayakawa et al. | |
| 2019/0076115 | A1* | 3/2019 | Bax | A61B 8/4218 |
| 2020/0323605 | A1* | 10/2020 | Tawil | A61B 5/0077 |
| 2021/0033243 | A1* | 2/2021 | Gold | F16M 11/2014 |
| 2021/0106309 | A1* | 4/2021 | Mesaros | A61B 8/4405 |
| 2021/0247019 | A1* | 8/2021 | Newville | F16M 11/121 |
| 2022/0054107 | A1 | 2/2022 | Onodera et al. | |
| 2022/0079562 | A1* | 3/2022 | Nakajima | A61B 8/467 |
| 2022/0370039 | A1* | 11/2022 | Zhao | A61B 8/46 |

FOREIGN PATENT DOCUMENTS

| | | | |
|---|---|---|---|
| CN | 111358489 | A | 7/2020 |
| CN | 212996496 | U | 4/2021 |
| JP | 2011-167305 | A | 9/2011 |
| JP | 6693784 | B2 | 5/2020 |
| WO | 2017/084019 | A1 | 5/2017 |

OTHER PUBLICATIONS

European Office Action dated May 7, 2025 issued in European Patent Application No. 24165730.3.

Office Action dated Feb. 19, 2026 issued in the corresponding European Patent Application No. 24165730.3. (Note: US20100204578A1 already submitted.).

* cited by examiner 810 (820, 830)
820 (840, 851, 852)

810 (820, 830)
820 (840, 851, 852)

ULTRASONIC IMAGING APPARATUS

CROSS-REFERENCE TO RELATED APPLICATION

This application is based on and claims priority under 35 U.S.C. § 119 to Korean Patent Application Nos. 10-2023-0047821 and 10-2023-0066500, respectively filed on Apr. 11, 2023, and May 23, 2023, in the Korean Intellectual Property Office, the disclosures of which are incorporated by reference herein in their entireties.

BACKGROUND

1. Field

The disclosure relates to an ultrasonic imaging apparatus, and more particularly, to a lifting arm that is multi-articulated to move a control panel up, down, left, right and diagonally with respect to a main body.

2. Description of the Related Art

In general, an ultrasonic imaging apparatus is a type of testing apparatus that emits ultrasonic waves into an object to be examined, such as a human body, by using a probe, and obtains an image by calculating a distance to the object by using a time difference between the transmitted ultrasonic waves and echoes reflected and returning from the inside of the object. Ultrasonic waves used in ultrasonic imaging apparatuses are known to be harmless to the human body. Thus, ultrasonic imaging apparatuses are particularly useful for medical purposes and have been widely used for detecting foreign substances in the human body, determining the extent of damage, and observing tumors or fetuses.

A main body of an ultrasonic imaging apparatus performs signal processing on ultrasonic echo signals received from the probe and generates ultrasound data regarding information on internal tissue of the object, and a control panel receives the data from the main body and provides the data to the user.

The control panel not only provides data as various values according to a user's needs, but is also movable up and down or forward and backward so that, even when the main body is far away from the user, the control panel may provide information in close proximity to the user at a user's desired location.

In existing ultrasonic imaging apparatuses, a control panel may be moved using a simple combination of a lift that performs an up and down movement and a swivel structure that performs a plane movement or using an arm that performs an up and down movement and a plane movement, and the control panel may be moved with 3 or 4 degrees of freedom depending on whether the control panel is able to rotate.

However, the control panel may have a considerable weight due to a display screen therein, operation switches, and wires arranged to receive a large amount of information from the main body. Thus, in case that a single member without joints or a plurality of short members are used to support the weight of the control panel, this limits an area over which the control panel is movable away from the main body, hinders a smooth movement of the control panel, and makes it difficult to adjust the movement of the control panel.

SUMMARY

The disclosure provides an ultrasonic imaging apparatus which includes a multi-articulated arm that allows a control panel to move up, down, left, right, or diagonally, so that a movement area of the control panel is increased and a smooth movement thereof is achieved, and a movement of the control panel is easily controlled by simultaneously constraining movements of the multi-articulated arms through a brake wire.

Additional aspects will be set forth in part in the description which follows and, in part, will be apparent from the description, or may be learned by practice of the presented embodiments.

According to an embodiment, an ultrasonic imaging apparatus includes a main body, a connecting unit configured to rotate and move with respect to the main body; and a control panel provided on an end of the connecting unit to be movable up, down, right, left, or diagonally while remaining horizontal with respect to the main body, wherein the connecting unit comprises: a first arm provided with four link bars forming a parallelogram in a same plane and configured to rotate and move with respect to the main body; and a second arm provided with four link bars forming a parallelogram in a plane provided independently of the first arm and configured to rotate and move with respect to the first arm.

The four link bars forming the parallelogram may include two horizontal bars arranged parallel to each other; and two vertical bars each being provided at two ends of the two horizontal bars, and the horizontal bars are configured to rotate about arm shafts provided on the vertical bars.

The main body may include a first connection frame provided to be connected to an end of the connection unit so that the connection unit rotates with respect to a first shaft, the control panel may include a second connection frame provided to be connected to another end of the connection unit so that the connection unit rotates with respect to a second shaft, and the connection unit may further include a third shaft is provided between the first arm and the second arm so that the first arm and the second arm rotate relative to each other.

The first arm and the second arm may be provided in a pair and included in each of a first lifting arm and a second lifting arm, and each of the first lifting arm and the second lifting arm may be configured to rotate about a first shaft with respect to the first connection frame provided on the main body at one end, and rotate about a second shaft with respect to a second connection frame provided on a bottom of the control panel at another end.

The connection unit may include a locking gas spring that is provided between the horizontal bars to compensate for weight during an up and down movement and to fix up and down positions, and the locking gas spring is provided in at least one of the first lifting arm or the second lifting arm.

The first connection frame may include a brake configured to prevent rotation of the first arm configured to rotate about the first shaft, and the second connection frame may include a brake configured to prevent rotation of the second arm configured to rotate about the second shaft.

The connection unit may further include a brake wire connected to the locking gas spring and the brake to determine whether the control panel is to be moved.

The first shaft, the second shaft, and the third shaft may be arranged parallel to one another and remain parallel even when an operation of the brake wire connected to the brake is released and thus the control panel is moved.

The ultrasonic imaging apparatus may further include an actuator connected to the brake wire and be configured to determine whether to operate the brake.

The arm shafts may be provided as two arm shaft on each of the vertical bars and located to be offset from each other so that the first arm and the second arm each form a parallelogram in a same plane.

The control panel may be further configured to rotate about the second shaft with the second connection frame provided on the bottom to perform a plane movement, and the second arm of any one of the first lift arm and the second lift arm may include a first rotating member connected to the second shaft, and the second arm of the other one of the first lift arm and the second lift arm may include a second rotating member not connected to the second shaft.

The first rotating member may have a cross-sectional area greater than a cross-sectional area of the second rotating member, and the second rotating member may be configured to support a bottom of the first rotating member and is connected to the first rotating member obliquely with respect to the second shaft so as to move with the first rotating member.

The third shaft may be provided as a plurality of third shafts each being connected to the vertical bar of the first arm and the vertical bar of the second arm so that the first arm and the second arm each rotate about the third shaft.

The connection unit may further include a brake configured to prevent the rotation of the first arm or the second arm.

The locking gas spring may be provided in the first lifting arm or the second lifting arm so that up and down positions are fixed by one of the first lifting arm and the second lifting arm, and the first lifting arm and the second lifting arm may be arranged asymmetrically to each other due to different lengths of the horizontal bar so that positions of the third shafts in the first lifting arm and the second lifting arm are different from each other.

According to an embodiment, an ultrasonic imaging apparatus may include a main body; a connecting unit configured to rotate and move with respect to the main body; a control panel provided on an end of the connecting unit and configured to be movable up, down, right, left, or diagonally while remaining horizontal with respect to the main body; and a locking unit configured to control a movement of the control panel.

The locking unit may include a locking gas spring configured to control an up and down movement of the control panel; and a brake configured to control forward and backward and left and right movements of the control panel, and is configured to simultaneously operate the locking gas spring and the brake.

The locking unit may include a locking device that is mechanically or electrically operated; and a link connected to the locking gas spring and the brake and moved by the locking device, and the locking gas spring and the brake receive forces in opposite directions to fix a position of the control panel.

The link may include a rotary link configured to rotate about one axis in response to an operation of the locking device; and a linear link configured to move along a straight line in response to the operation of the locking device, the rotary link and the linear link are connected to each other in a partially overlapping manner, so that an operation of one of the rotary link and the linear link causes an operation of the other link, and at least one of the rotary link or the linear link is connected to the locking device and is operated simultaneously by the operation of the locking device.

The locking device may include an actuator configured to move the link when electrically operated; and a drive shaft corresponding to the one axis of the link.

The ultrasonic imaging apparatus may further include a gas spring cable configured to move the locking gas spring, wherein the gas spring cable has one end connected to the locking gas spring and another end connected to the link to operate the locking gas spring due to the operation of the locking device.

BRIEF DESCRIPTION OF THE DRAWINGS

The above and other aspects, features, and advantages of certain embodiments will be more apparent from the following description taken in conjunction with the accompanying drawings, in which.

Figure 4:
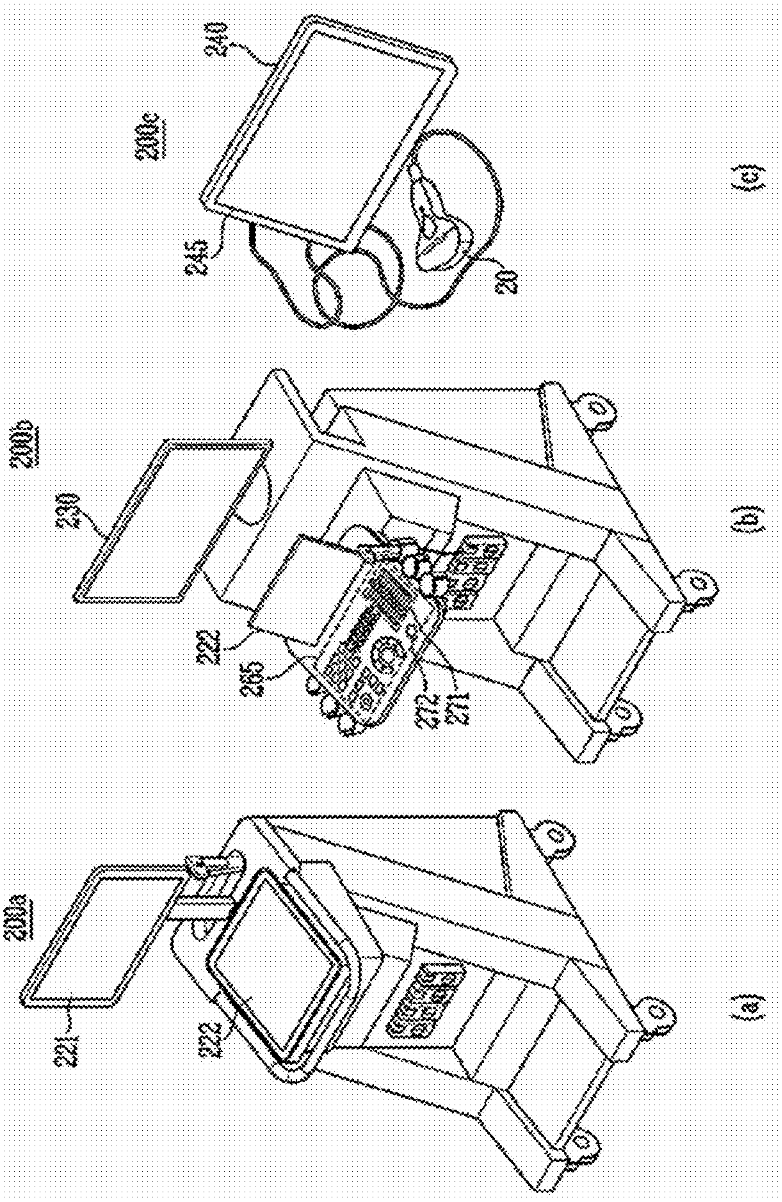
Figure 5:
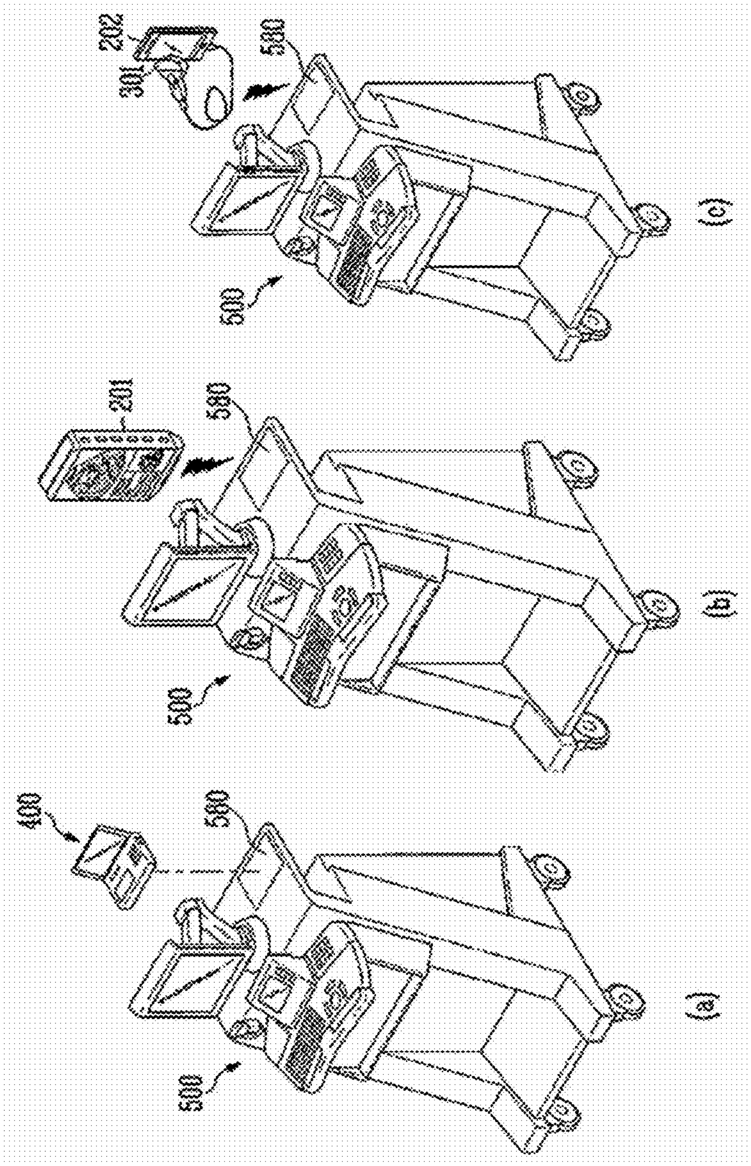
Figure 6:
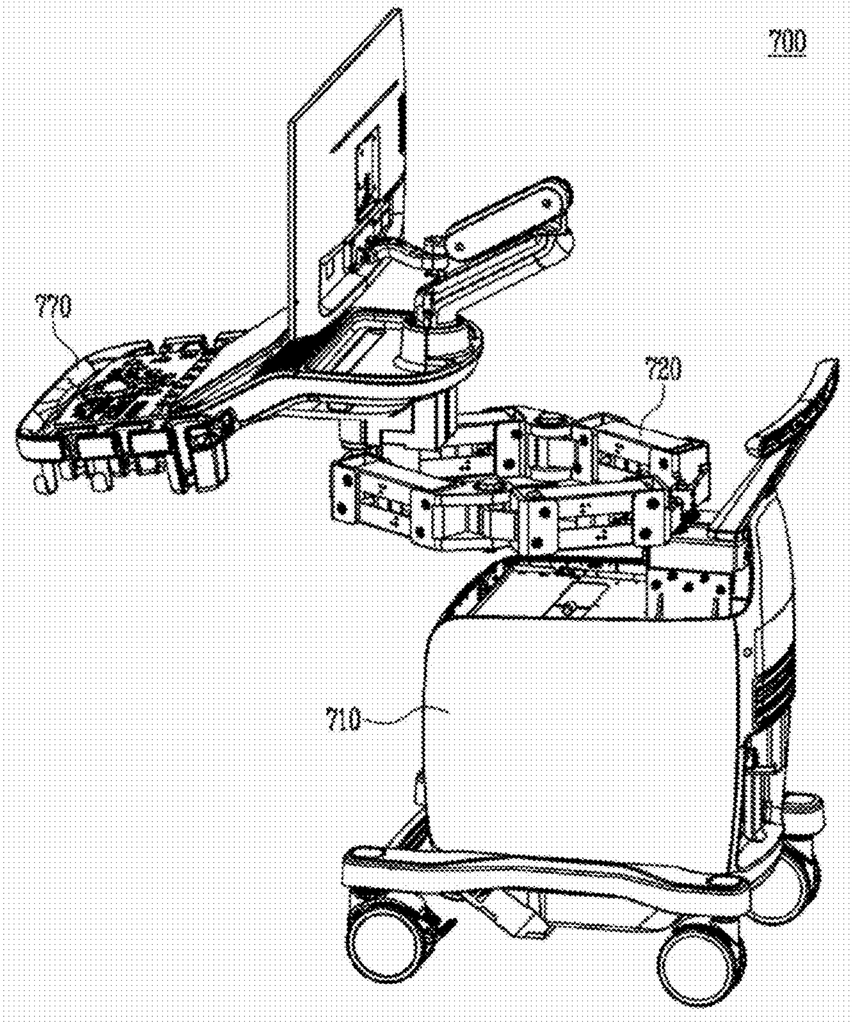
Figure 7:
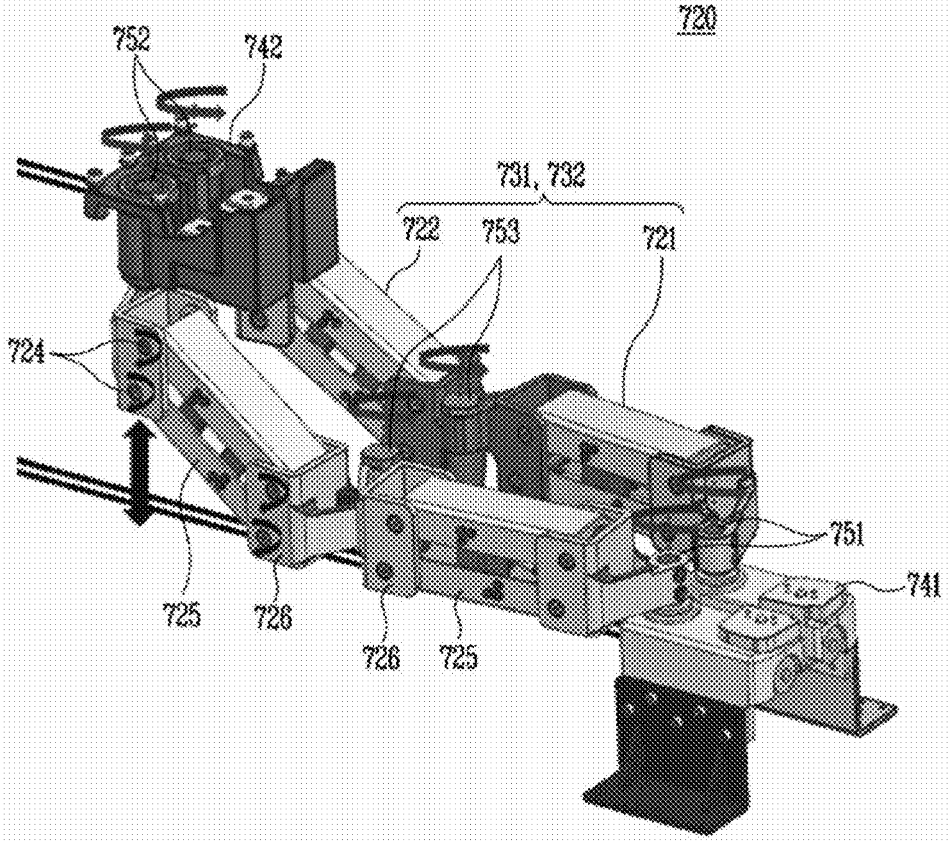
Figure 8A:
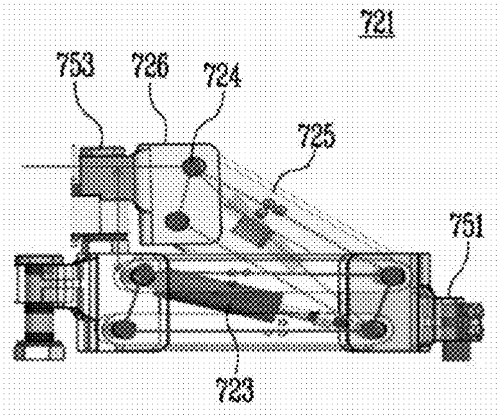
Figure 8B:
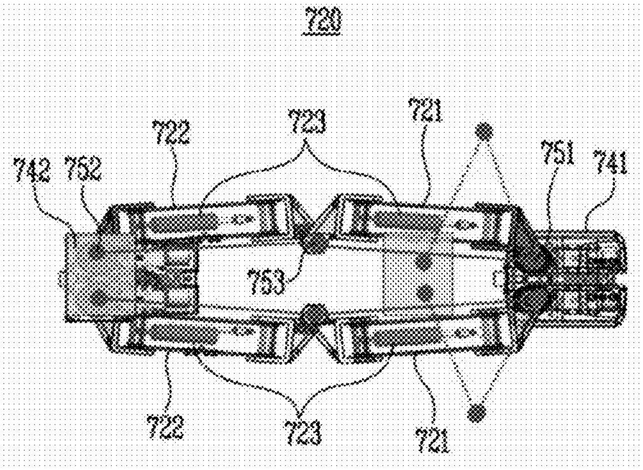
Figure 9:
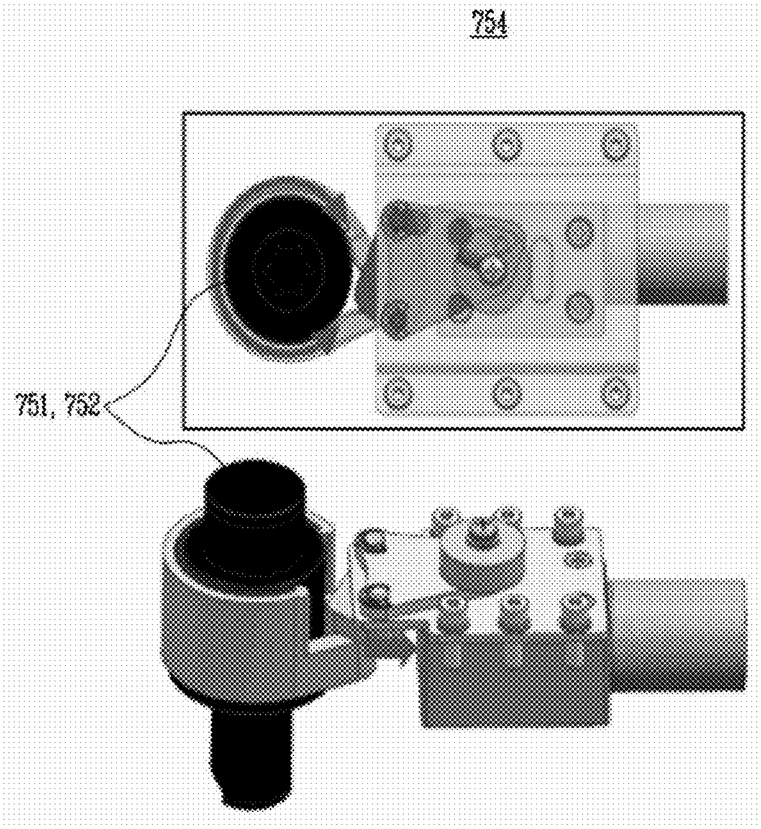
Figure 10A:
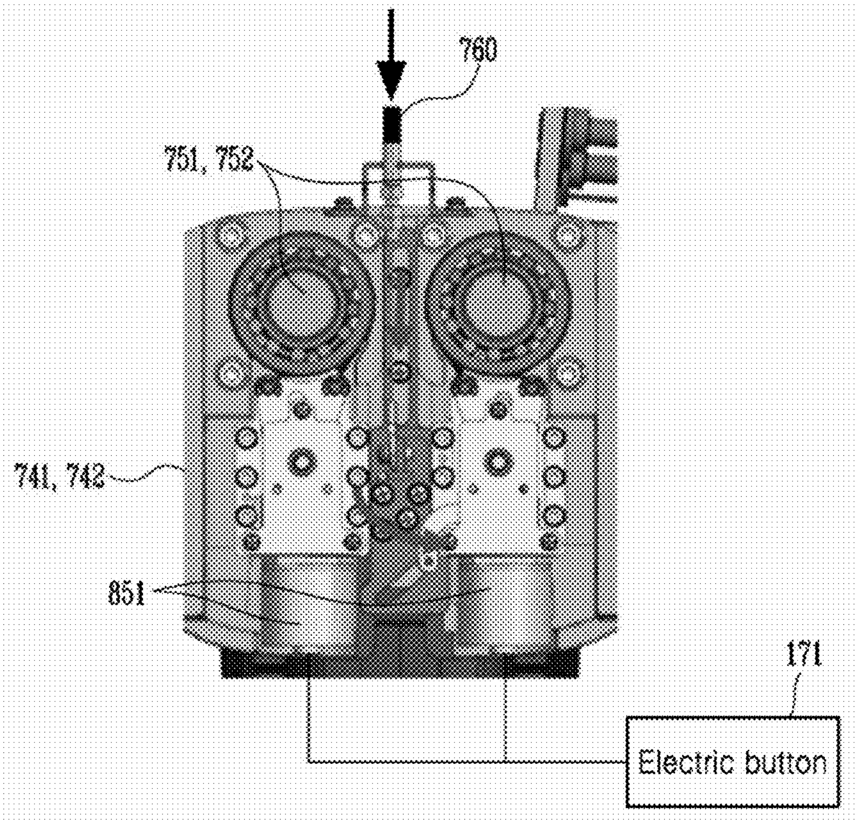
Figure 10B:
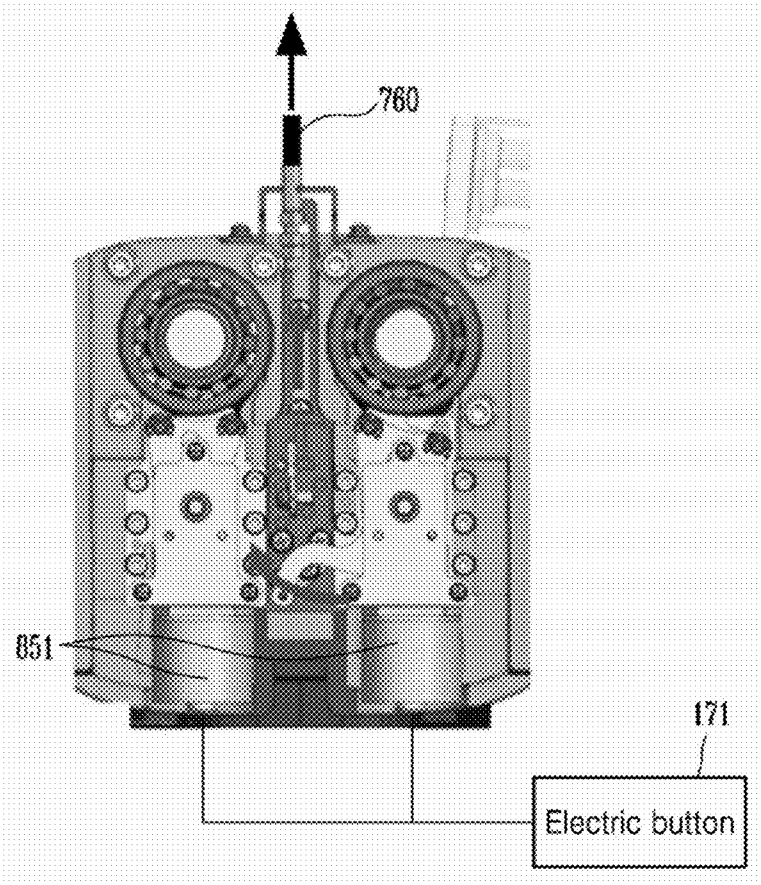
Figure 11A:
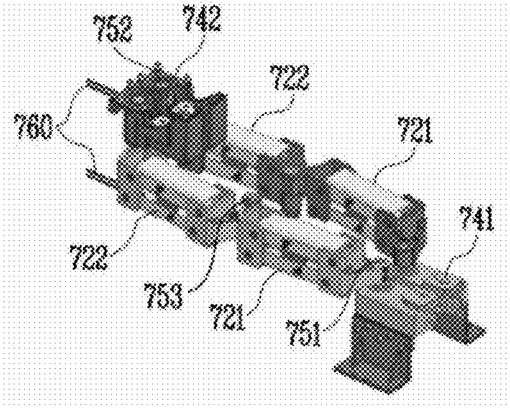
Figure 11B:
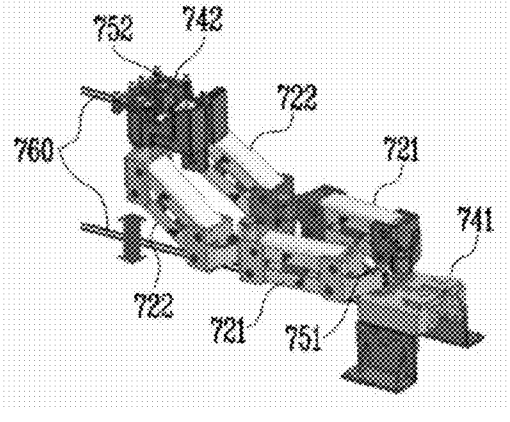
Figure 11C:
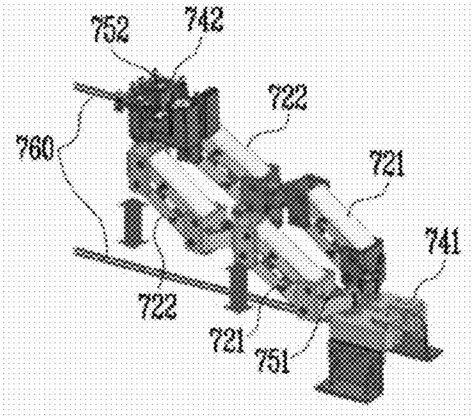
Figure 12A:
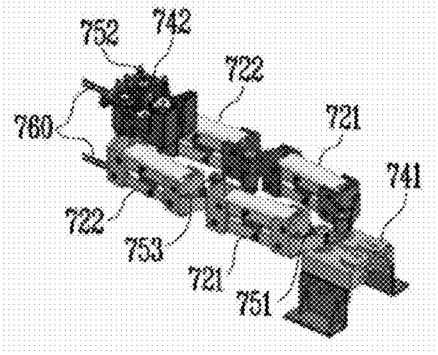
Figure 12B:
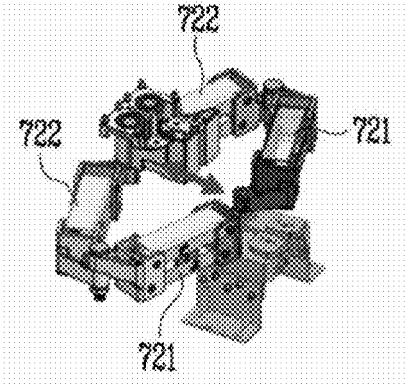
Figure 12C:
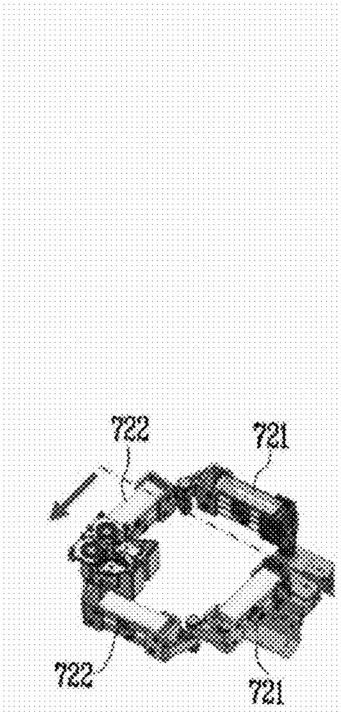
Figure 12D:
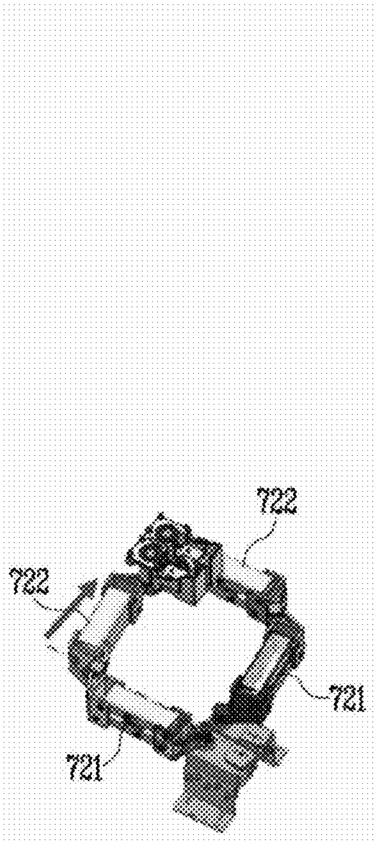
Figure 13A:
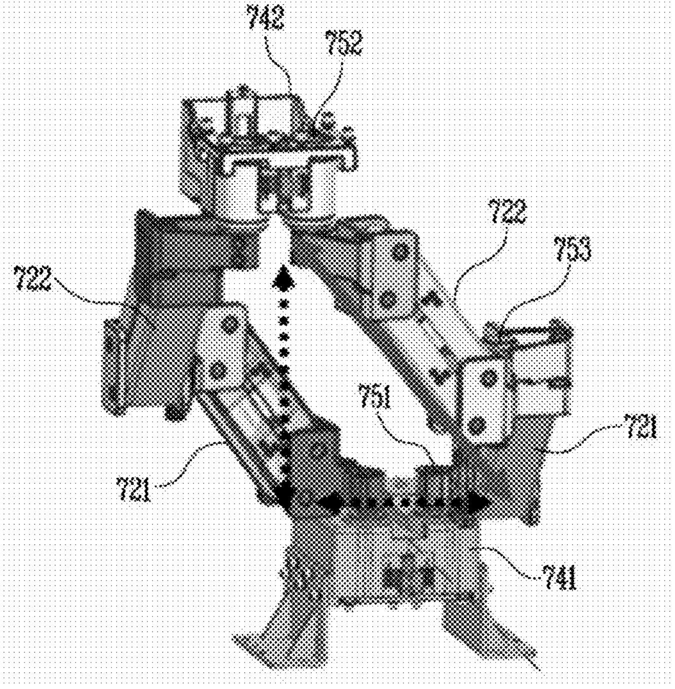
Figure 13B:
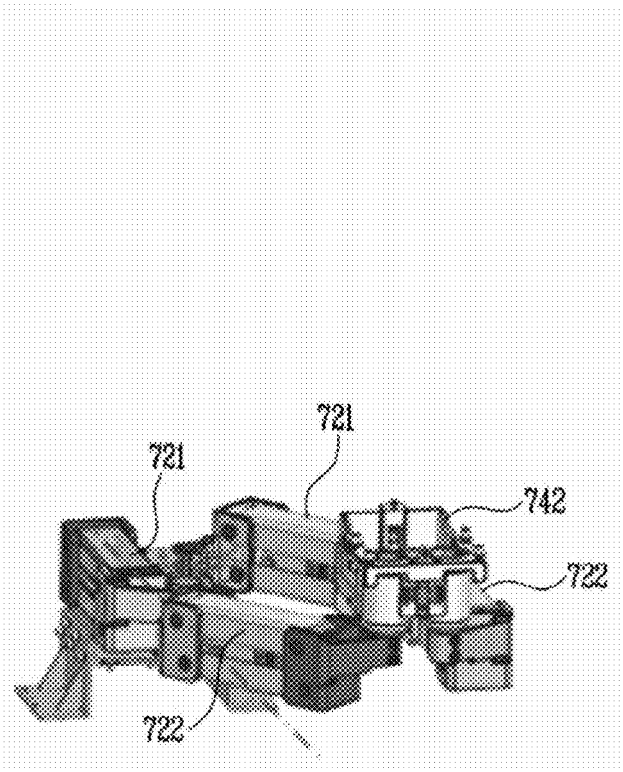
Figure 14:
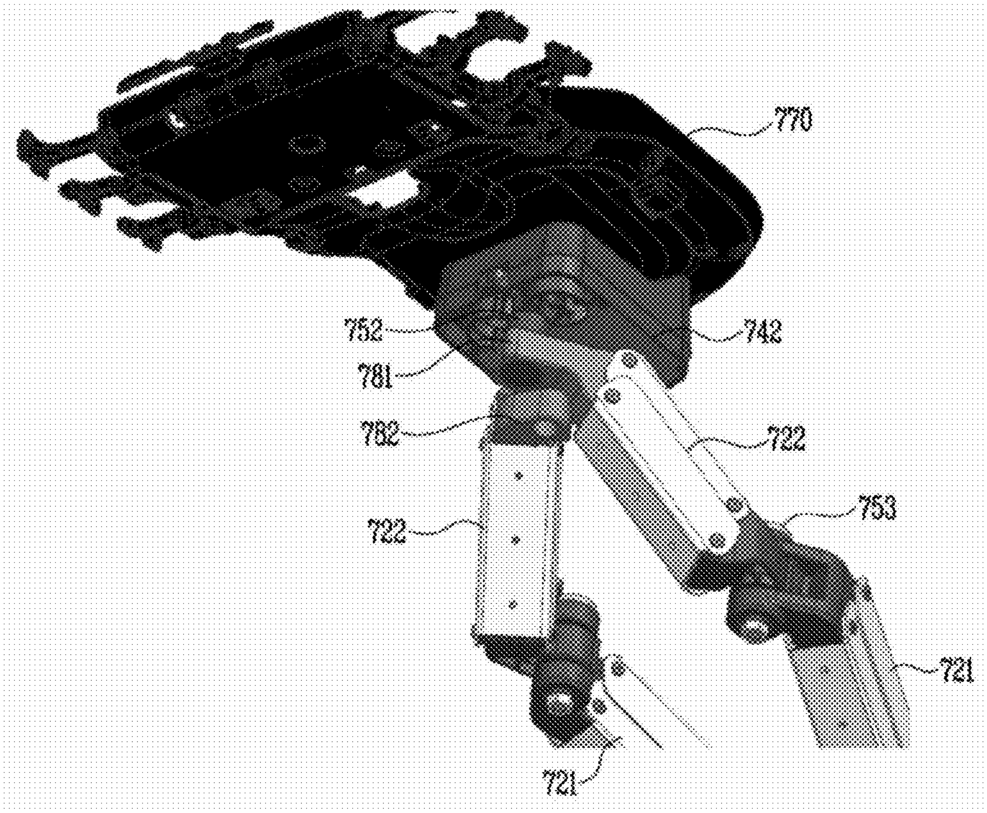
Figure 15:
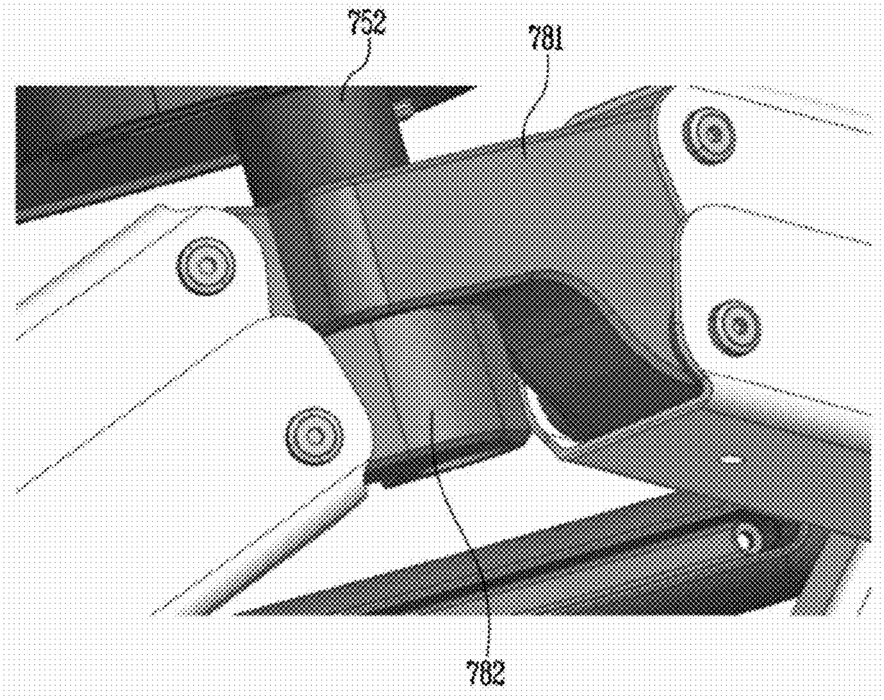
Figure 16:
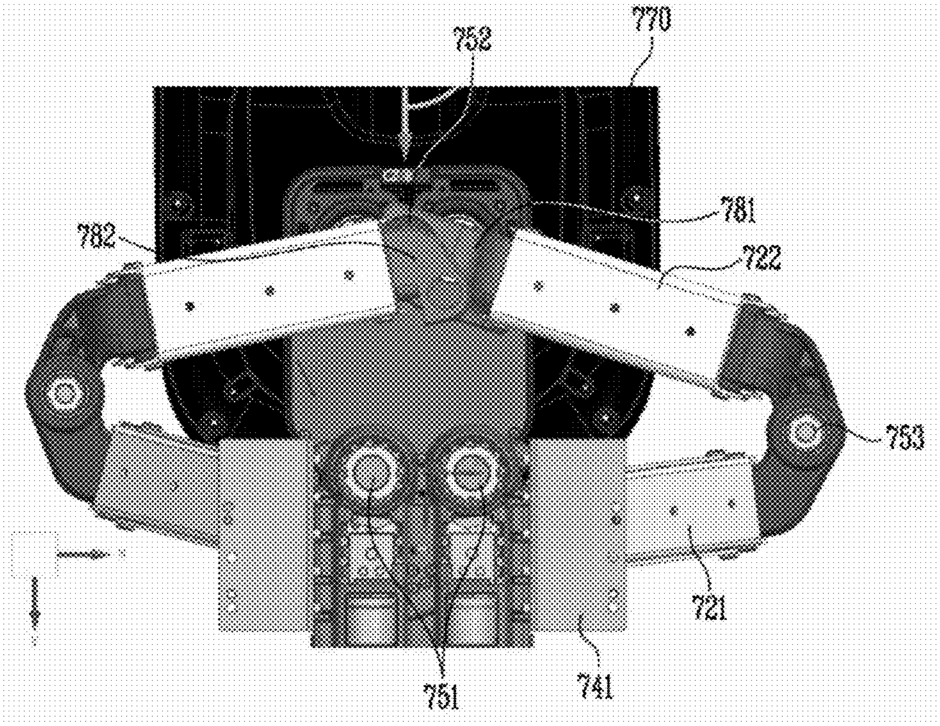
Figure 17:
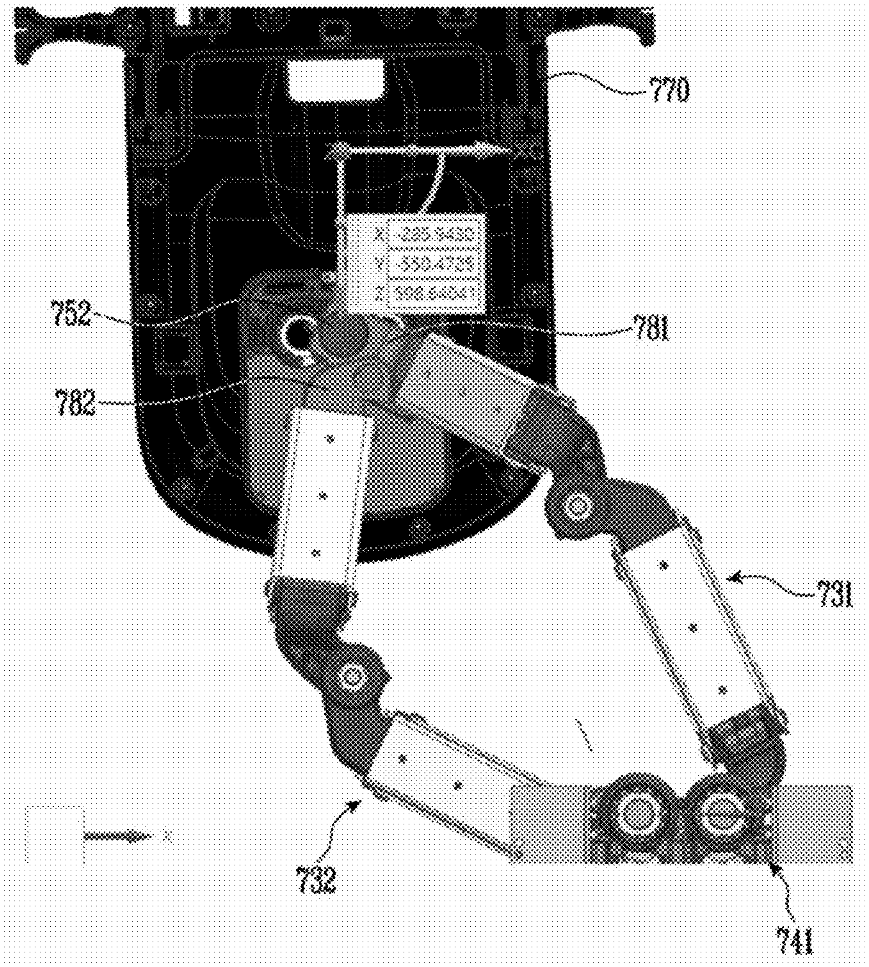
Figure 18:
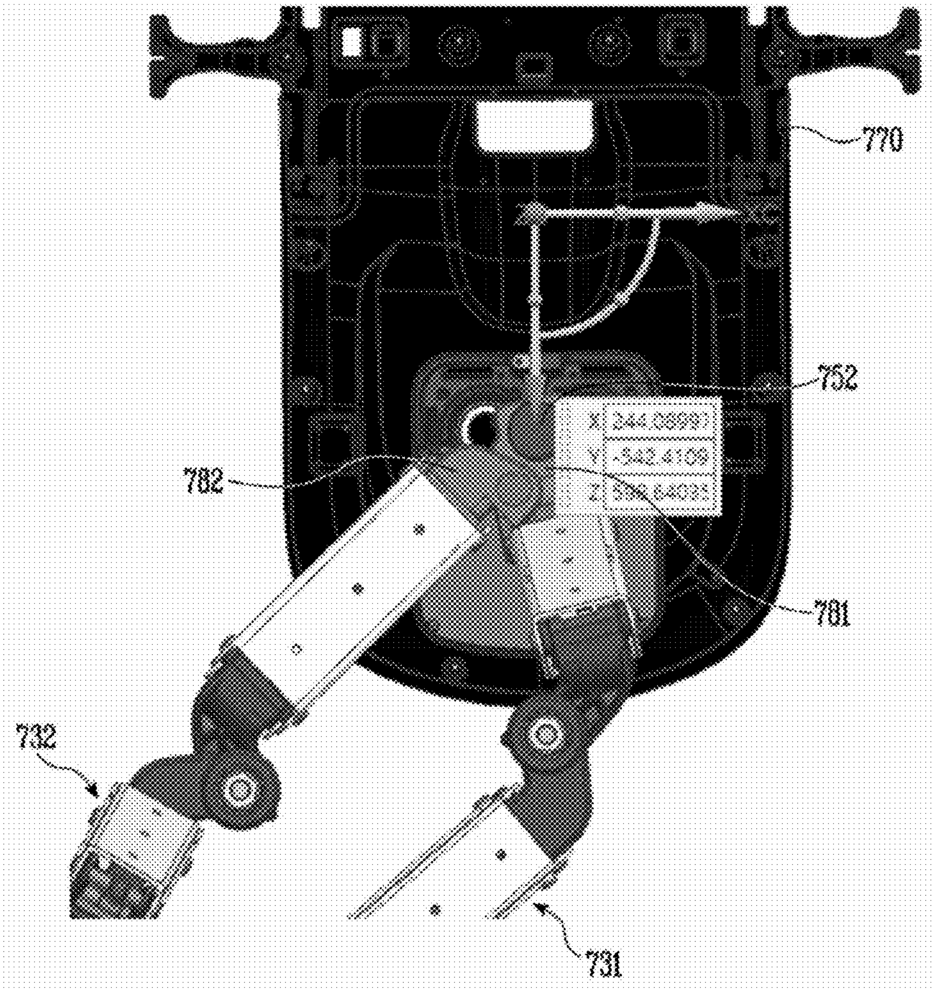
Figure 19A:
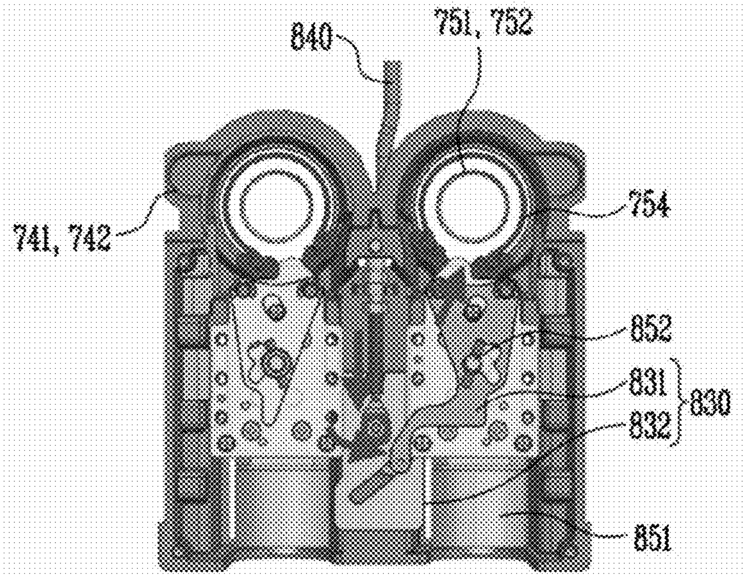
Figure 19B:
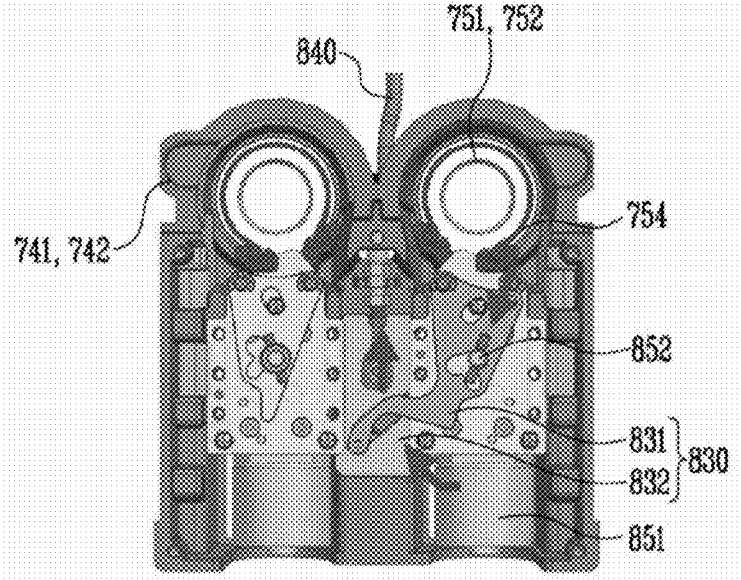
Figure 20A:
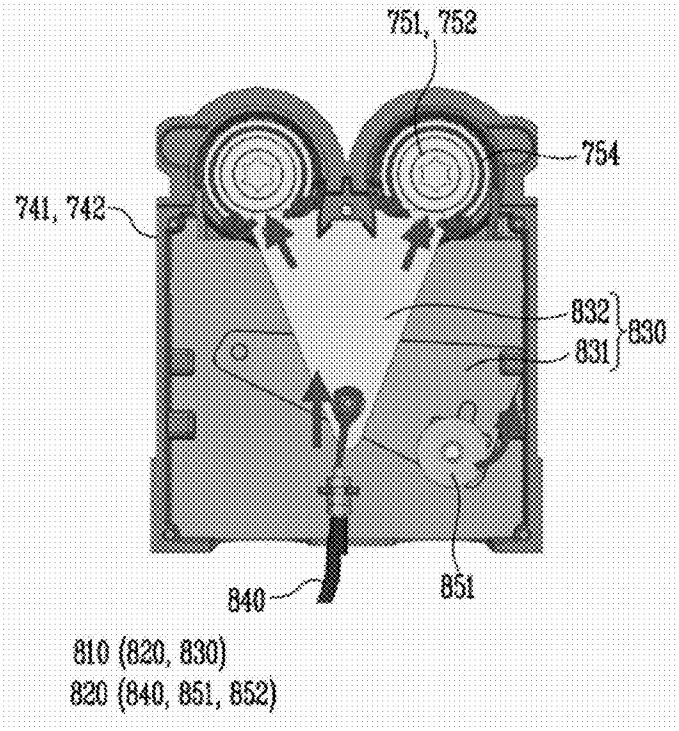
Figure 20B:
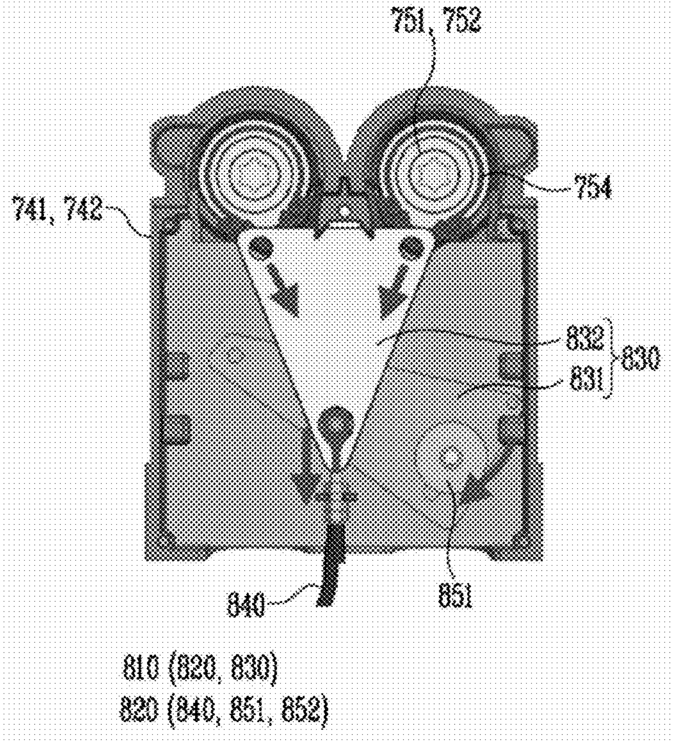
Figure 21A:
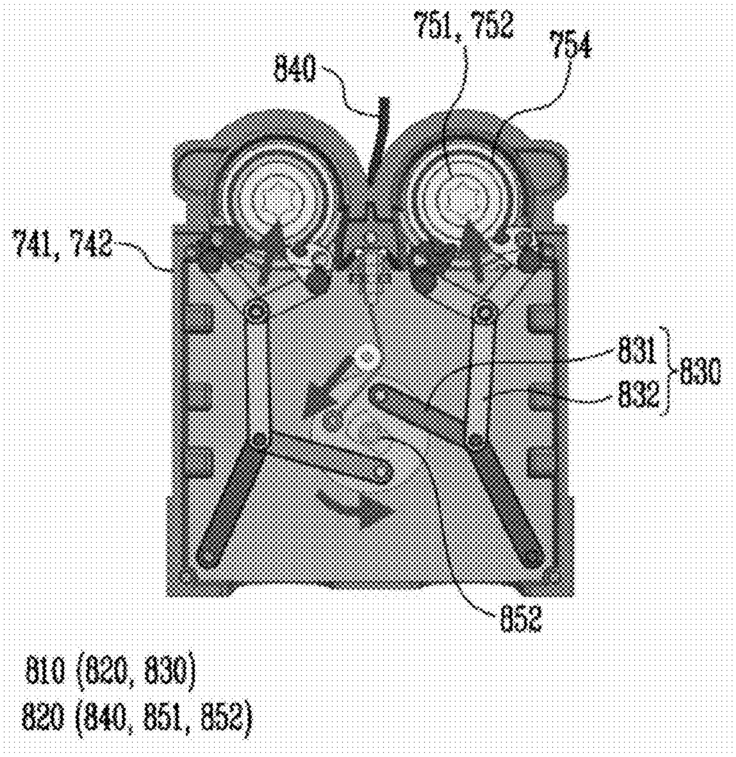
Figure 21B:
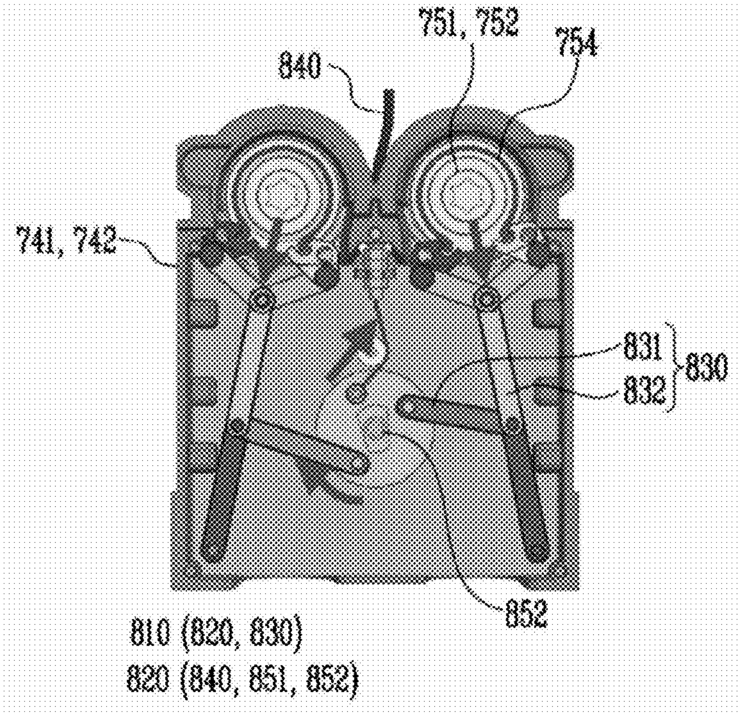
Figure 22A:
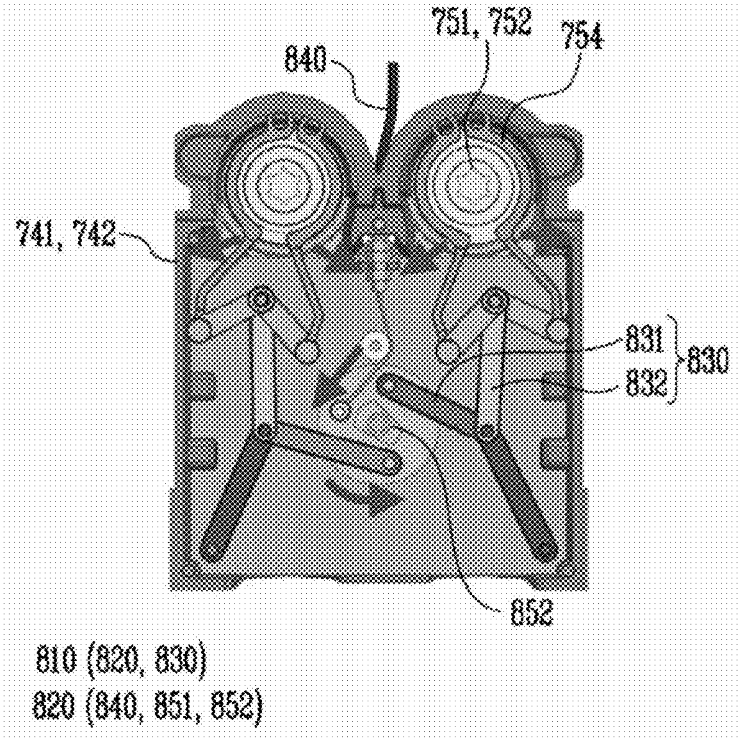
Figure 22B:
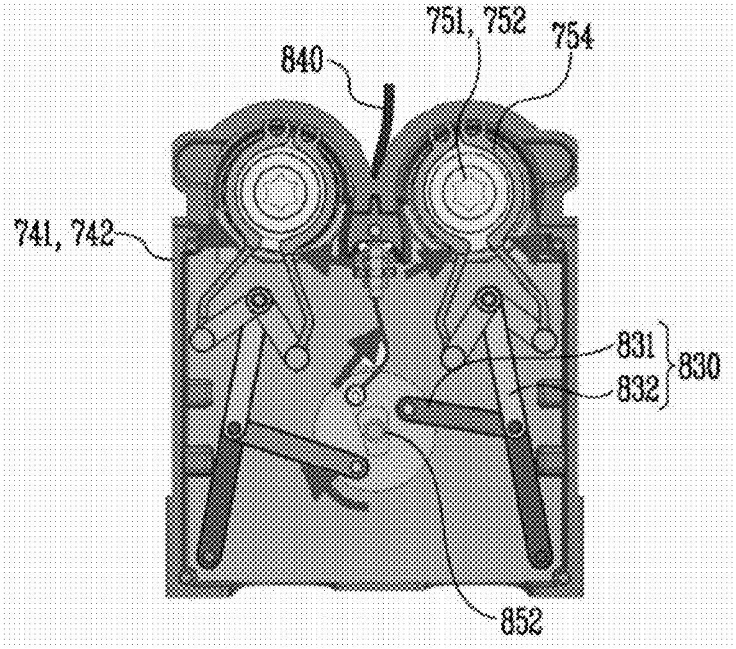
Figure 23A:
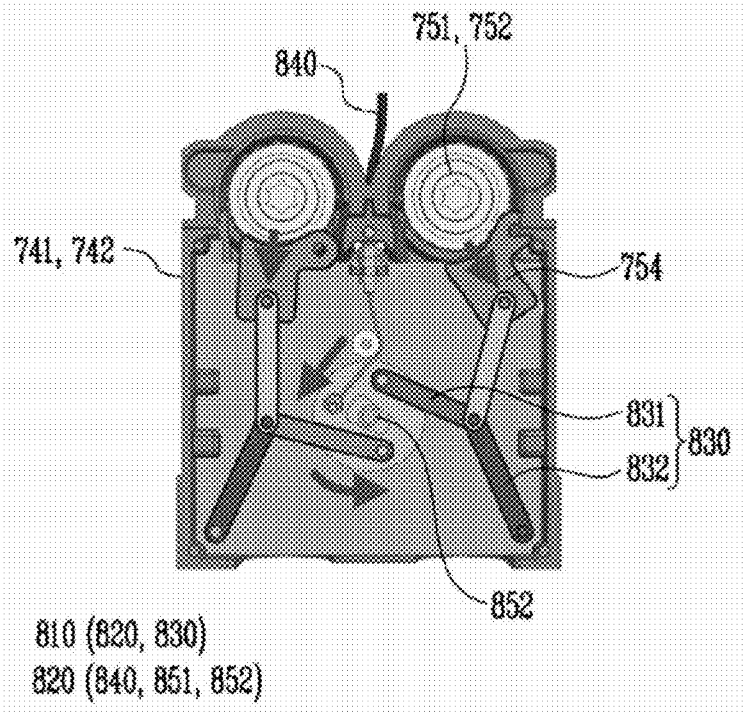
Figure 23B:
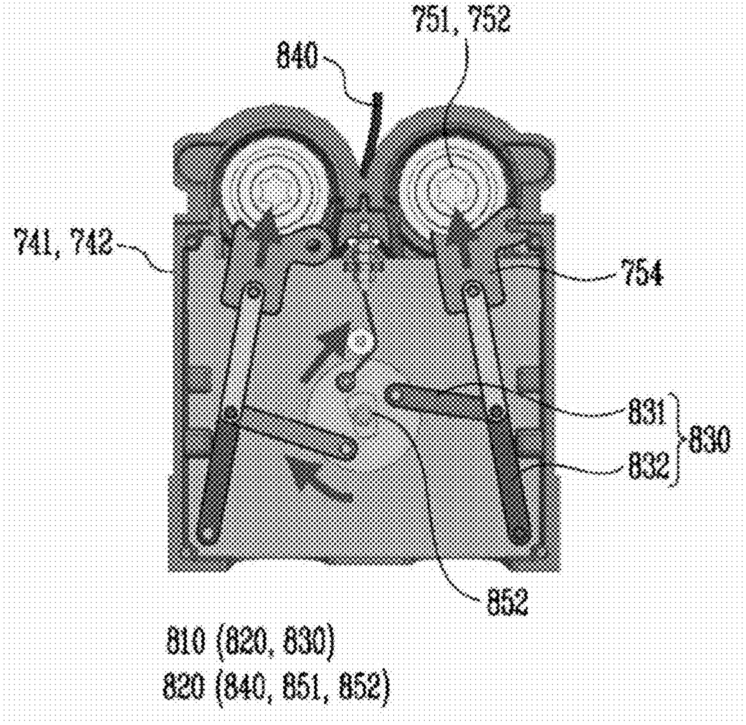
Figure 24A:
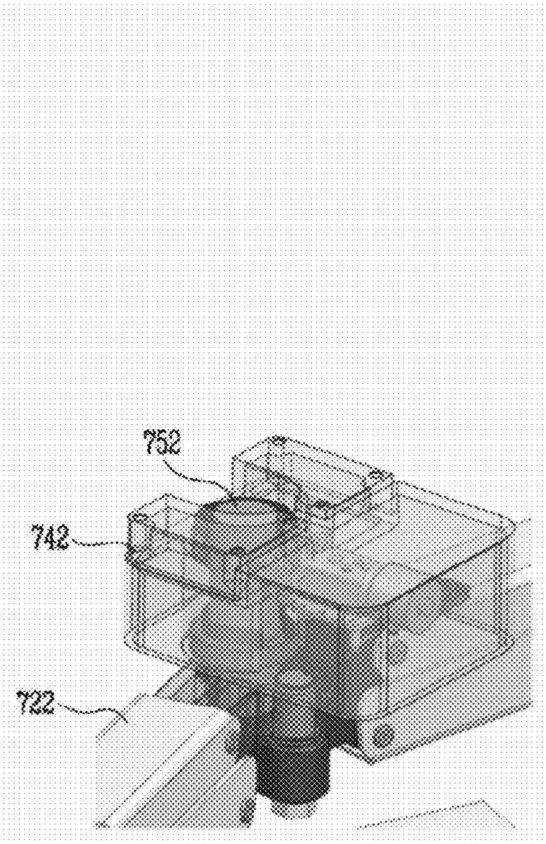
Figure 24B:
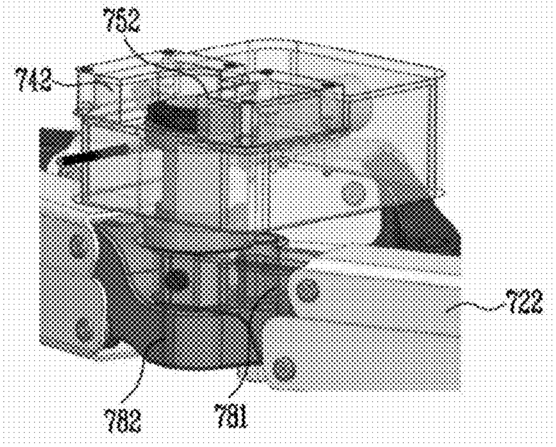
Figure 25A:
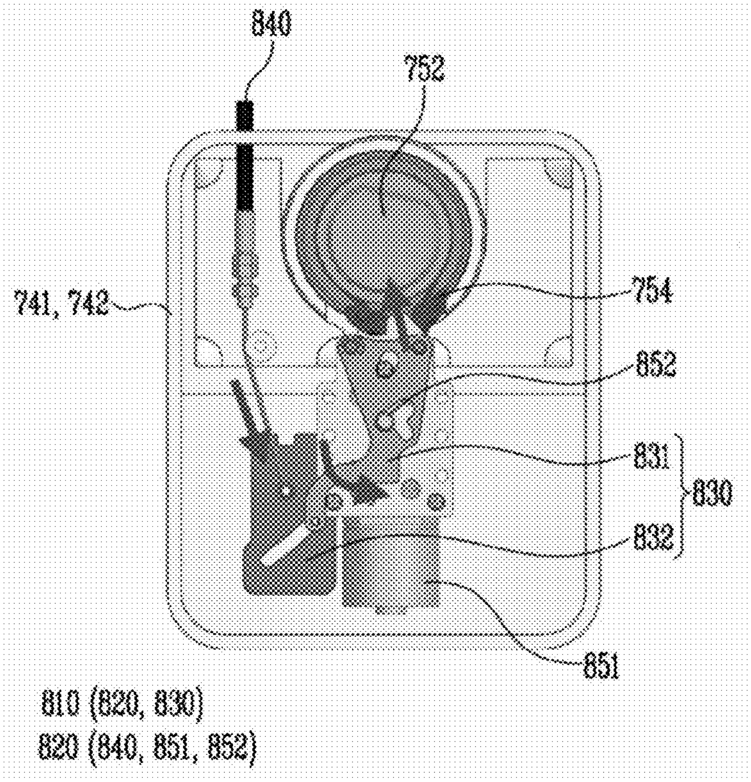
Figure 25B:
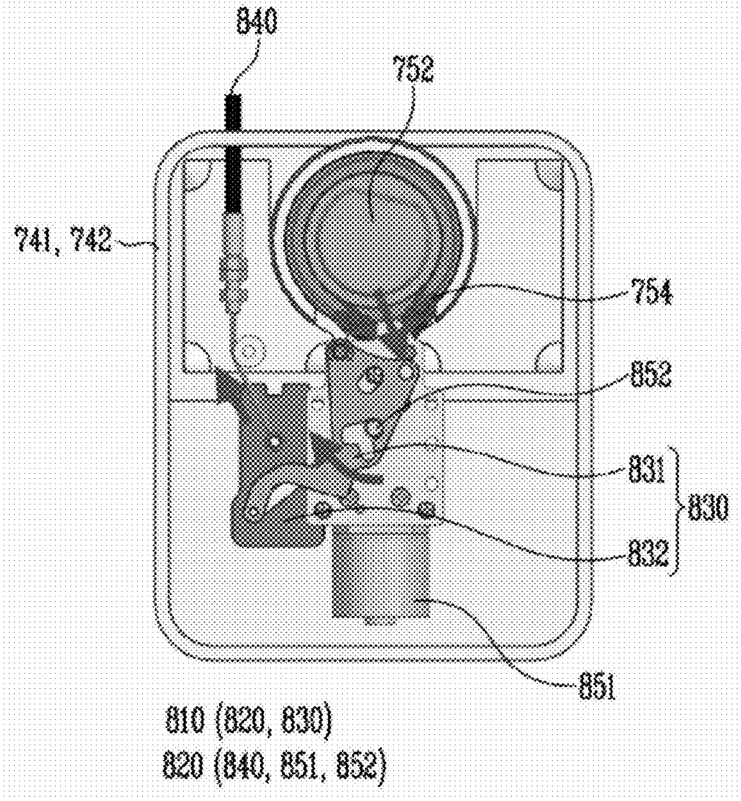
Figure 26:
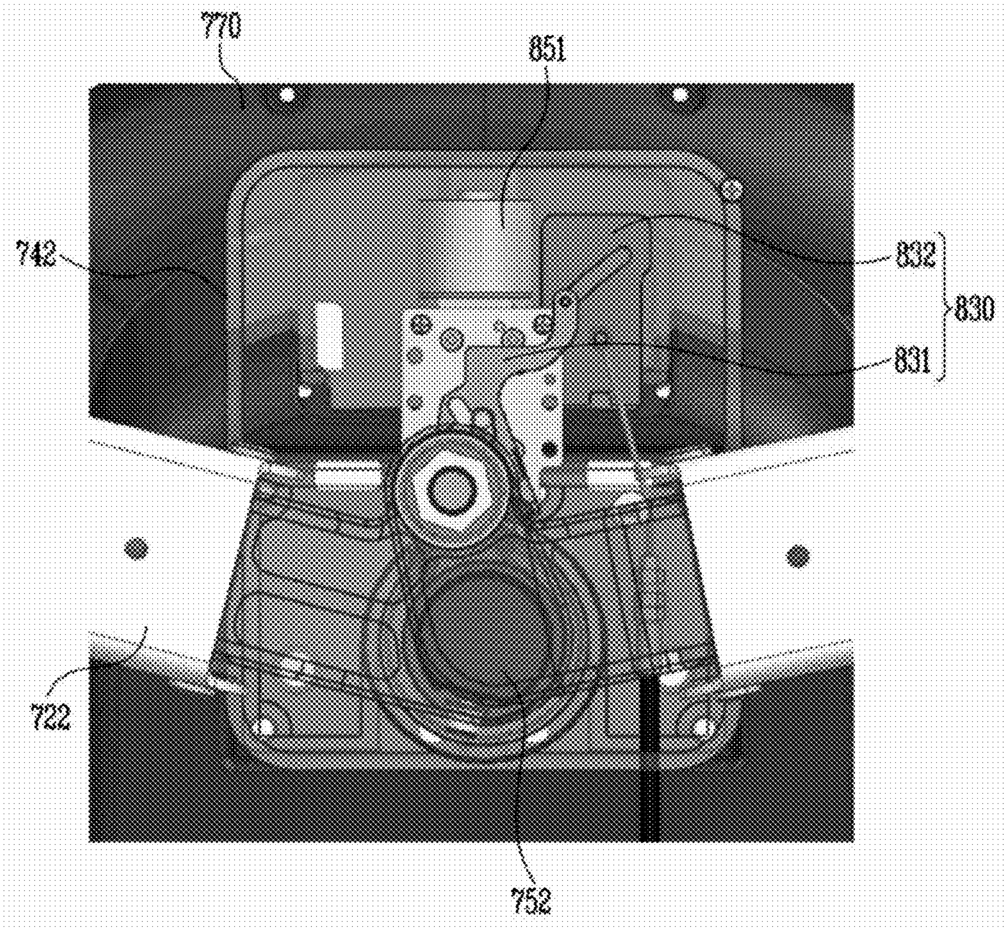
Figure 27:
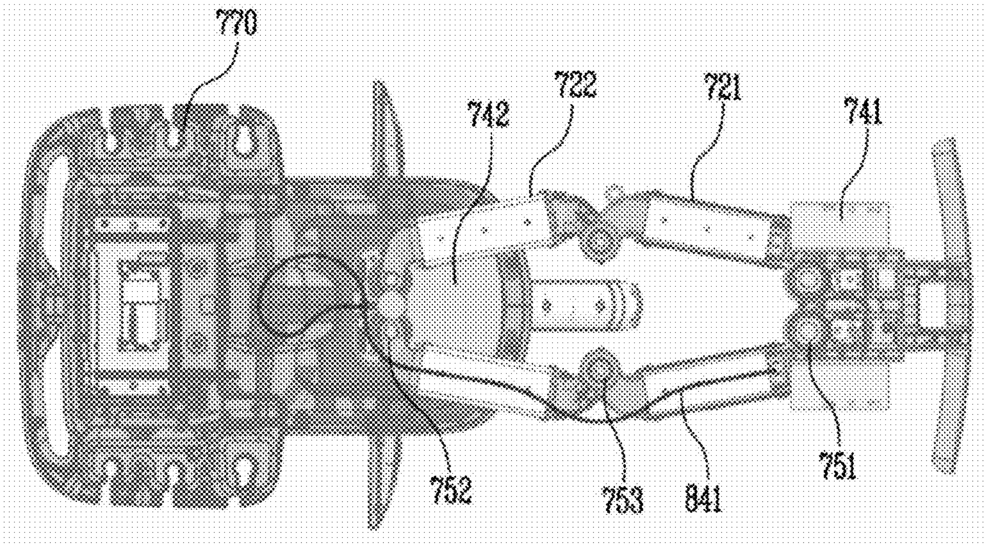
Figure 28:
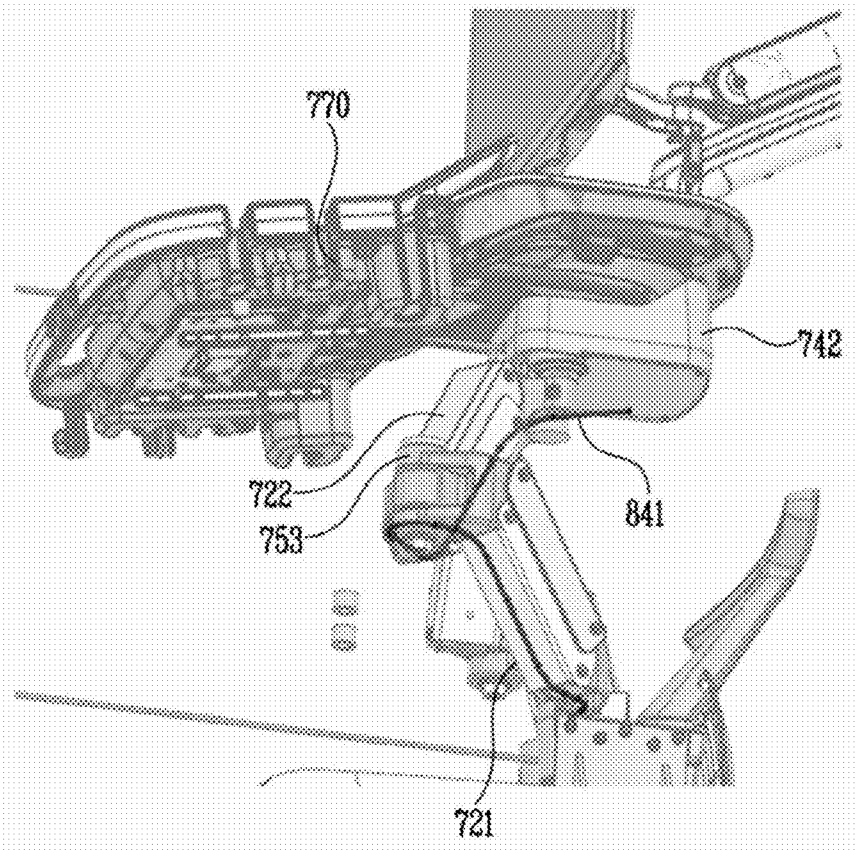
Figure 29:
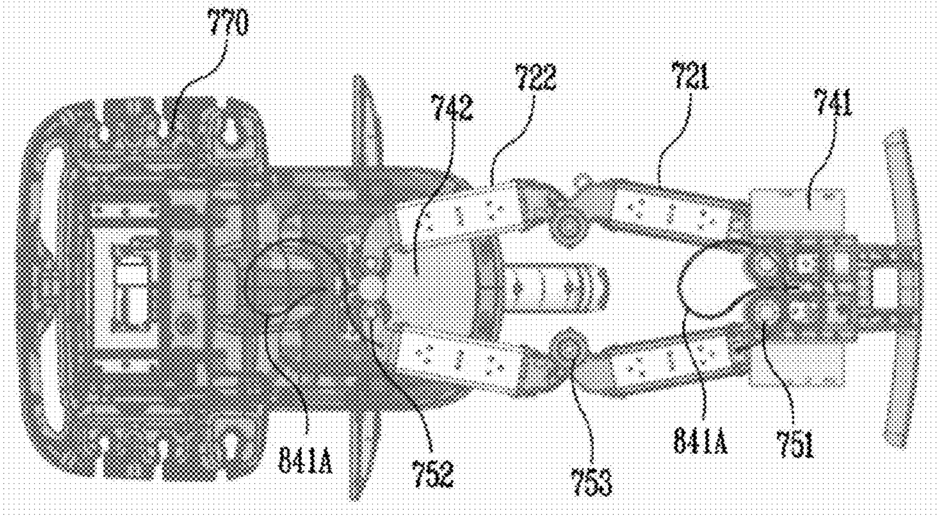
Figure 30:
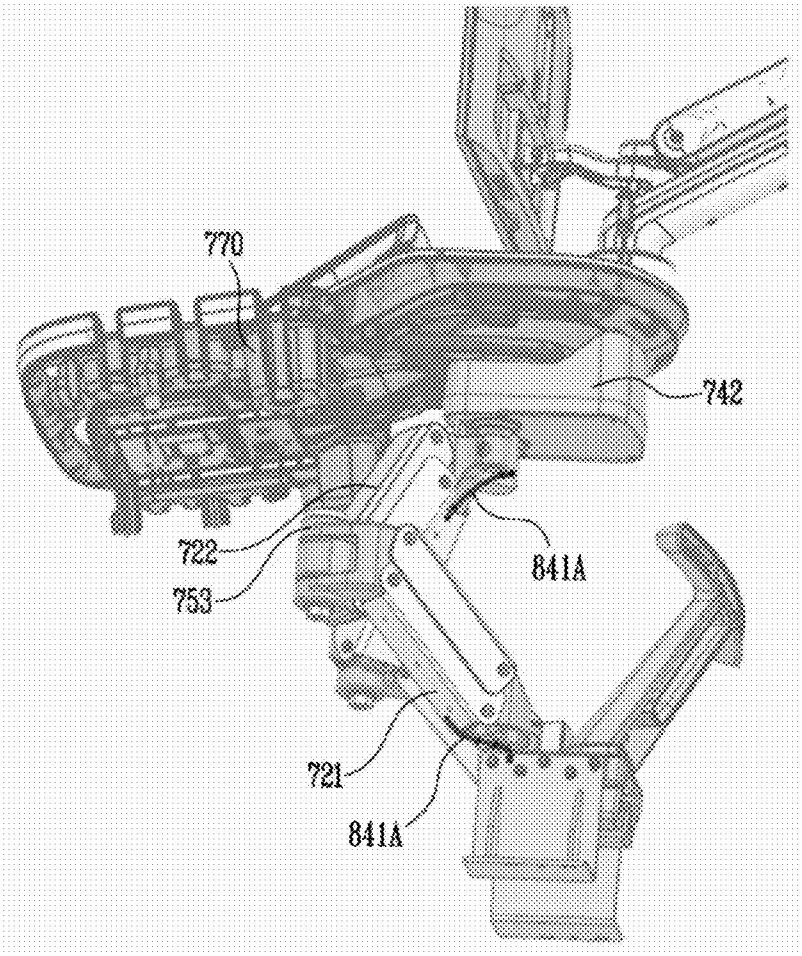

(a) to (c) of FIG. 4 are perspective views of ultrasonic imaging apparatuses according to at least one embodiment;

(a) to (c) of FIG. 5 are perspective views of an ultrasonic imaging apparatus according to at least one embodiment;

FIG. 6 is a perspective view of an ultrasonic imaging apparatus according to a first embodiment;

FIG. 7 is an enlarged perspective view illustrating the ultrasonic imaging apparatus according to the first embodiment;

FIG. 8A is a close-up perspective view of a first arm or a second arm of the ultrasonic imaging apparatus 700 according to the first embodiment;

FIG. 8B is a close-up perspective view of a first lifting arm or a second lifting arm of the ultrasonic imaging apparatus according to the first embodiment;

FIG. 9 is a diagram illustrating a process in which a brake is operated in the ultrasonic imaging apparatus according to the first embodiment;

FIG. 10A is a diagram illustrating a process in which a brake wire is operated in the ultrasonic imaging apparatus according to the first embodiment;

FIG. 10B is a diagram illustrating a process in which the brake wire is operated in the ultrasonic imaging apparatus 700 according to the first embodiment;

FIG. 11A is a diagram illustrating a movement of a connecting unit for moving a control panel up and down in the ultrasonic imaging apparatus according to the first embodiment;

FIG. 11B is a diagram illustrating the movement of the connecting unit for moving the control panel up and down in the ultrasonic imaging apparatus according to the first embodiment;

FIG. 11C is a diagram illustrating the movement of the connecting unit for moving the control panel up and down in the ultrasonic imaging apparatus according to the first embodiment;

FIG. 12A is a diagram illustrating a movement of the connecting unit for moving the control panel forward and backward and left and right in the ultrasonic imaging apparatus according to the first embodiment;

FIG. 12B is a diagram illustrating the movement of the connecting unit for moving the control panel forward and backward and left and right in the ultrasonic imaging apparatus according to the first embodiment;

FIG. 12C is a diagram illustrating the movement of the connecting unit for moving the control panel forward and backward and left and right in the ultrasonic imaging apparatus according to the first embodiment;

FIG. 12D is a diagram illustrating the movement of the connecting unit for moving the control panel forward and backward and left and right in the ultrasonic imaging apparatus according to the first embodiment;

FIG. 13A is a diagram illustrating a movement of the connecting unit for diagonally moving the control panel in the ultrasonic imaging apparatus according to the first embodiment;

FIG. 13B is a diagram illustrating the movement of the connecting unit for diagonally moving the control panel in the ultrasonic imaging apparatus according to the first embodiment;

FIG. 14 is a diagram illustrating the connection of a second shaft in an ultrasonic imaging apparatus according to a second embodiment;

FIG. 15 is a diagram illustrating the connection of the second shaft in the ultrasonic imaging apparatus according to the second embodiment;

FIG. 16 is a diagram illustrating a movement of a connecting unit for diagonally moving a control panel in the ultrasonic imaging apparatus according to the second embodiment;

FIG. 17 is a diagram illustrating the movement of the connecting unit for diagonally moving the control panel in the ultrasonic imaging apparatus according to the second embodiment;

FIG. 18 is a diagram illustrating the movement of the connecting unit for diagonally moving the control panel in the ultrasonic imaging apparatus according to the second embodiment;

FIG. 19A is a cross-sectional view illustrating an operation of a locking unit in an ultrasonic imaging apparatus according to a 1st-1 embodiment;

FIG. 19B is a cross-sectional view illustrating an operation of the locking unit in the ultrasonic imaging apparatus according to the 1st-1 embodiment;

FIG. 20A is a cross-sectional view illustrating an operation of a locking unit in an ultrasonic imaging apparatus according to a 1st-2 embodiment;

FIG. 20B is a cross-sectional view illustrating an operation of the locking unit in the ultrasonic imaging apparatus according to the 1st-2 embodiment;

FIG. 21A is a cross-sectional view illustrating an operation of a locking unit in an ultrasonic imaging apparatus according to a 1st-3 embodiment;

FIG. 21B is a cross-sectional view illustrating an operation of the locking unit in the ultrasonic imaging apparatus according to the 1st-3 embodiment;

FIG. 22A is a cross-sectional view illustrating an operation of a locking unit in an ultrasonic imaging apparatus according to a 1st-4 embodiment;

FIG. 22B is a cross-sectional view illustrating an operation of the locking unit in the ultrasonic imaging apparatus according to the 1st-4 embodiment;

FIG. 23A is a cross-sectional view illustrating an operation of a locking unit in an ultrasonic imaging apparatus according to a 1st-5 embodiment;

FIG. 23B is a cross-sectional view illustrating an operation of the locking unit in the ultrasonic imaging apparatus according to the 1st-5 embodiment;

FIG. 24A is a close-up perspective view of the ultrasonic imaging apparatus according to the second embodiment;

FIG. 24B is a close-up perspective view of the ultrasonic imaging apparatus according to the second embodiment;

FIG. 25A is a cross-sectional view illustrating an operation of a locking unit in an ultrasonic imaging apparatus according to a 2nd-1 embodiment;

FIG. 25B is a cross-sectional view illustrating an operation of the locking unit in the ultrasonic imaging apparatus according to the 2nd-1 embodiment;

FIG. 26 is a close-up perspective view of a second connection frame provided on a bottom of a control panel in the ultrasonic imaging apparatus according to the 2nd-1 embodiment;

FIG. 27 is a close-up perspective view of first arrangement of a gas spring cable in an ultrasonic imaging apparatus, according to an embodiment;

FIG. 28 is a close-up perspective view of the first arrangement of the gas spring cable in the ultrasonic imaging apparatus, according to the embodiment;

FIG. 29 is a close-up perspective view of second arrangement of the gas spring cable in the ultrasonic imaging apparatus, according to an embodiment; and FIG. 30 is a close-up perspective view of the second arrangement of the gas spring cable in the ultrasonic imaging apparatus, according to the embodiment.

DETAILED DESCRIPTION

Throughout the disclosure, the expression "at least one of a, b or c" indicates only a, only b, only c, both a and b, both a and c, both b and c, all of a, b, and c, or variations thereof.

The present specification describes principles of the disclosure and sets forth embodiments thereof to clarify the scope of the disclosure and to allow one of ordinary skill in the art to implement the disclosure.

The embodiments may be implemented in various forms.

Throughout the specification, it will be understood that when a part is referred to as being "connected" or "coupled" to another part, it may be directly connected to or indirectly coupled to the other part, and the indirect connection includes a connection via a wireless communication network.

The terms used herein are for the purpose of describing an embodiment and is not intended to limit the disclosure.

As used herein, singular forms are intended to include the plural forms as well, unless the context clearly indicates otherwise.

It will be further understood that the terms "comprises" and/or "includes" when used in this specification, specify the presence of stated features, numbers, steps, operations, elements, components, or combinations thereof, but do not preclude the presence or addition of one or more other features, numbers, steps, operations, elements, components, or combinations thereof.

It will be understood that, although the terms including an ordinal number such as "first", "second", etc. may be used herein to describe various elements or components, these elements or components should not be limited by the terms, and the terms are only used to distinguish one element or component from another element or component.

For example, as used herein, a first element or component may be termed a second element or component without departing from the scope of the disclosure, and similarly, a second element or component may be termed a first element or component.

Furthermore, terms such as "portion", "device", "block", "member", and "module" used herein may refer to a unit for processing at least one function or operation.

For example, the terms may denote at least one hardware element such as a field-programmable gate array (FPGA) or an application-specific integrated circuit (ASIC), at least one software stored in a memory, or at least one process processed by a processor.

Reference numerals assigned to respective operations are used to identify the corresponding operations, and these reference numerals are not intended to indicate the order of the operations, and the operations may be performed in an order different from the specified order unless the context clearly indicates otherwise.

Furthermore, in the present specification, an image may include any medical image obtained by a medical imaging apparatus such as a magnetic resonance imaging (MRI) apparatus, a computed tomography (CT) apparatus, an ultrasonic imaging apparatus, or an X-ray apparatus, and the image may provide or control ultrasound imaging and medical images from modalities other than ultrasound imaging.

Also, as used herein, an 'object' is a target to be imaged, and may include a human, an animal, or a part thereof.

For example, the object may include a part of a body (organ, tissue, or the like), or a phantom.

Throughout the specification, an "ultrasound image" refers to an image of an object processed based on ultrasound signals transmitted to the object and reflected therefrom.

Hereinafter, embodiments will be described in detail with reference to the accompanying drawings.

Figure 1:
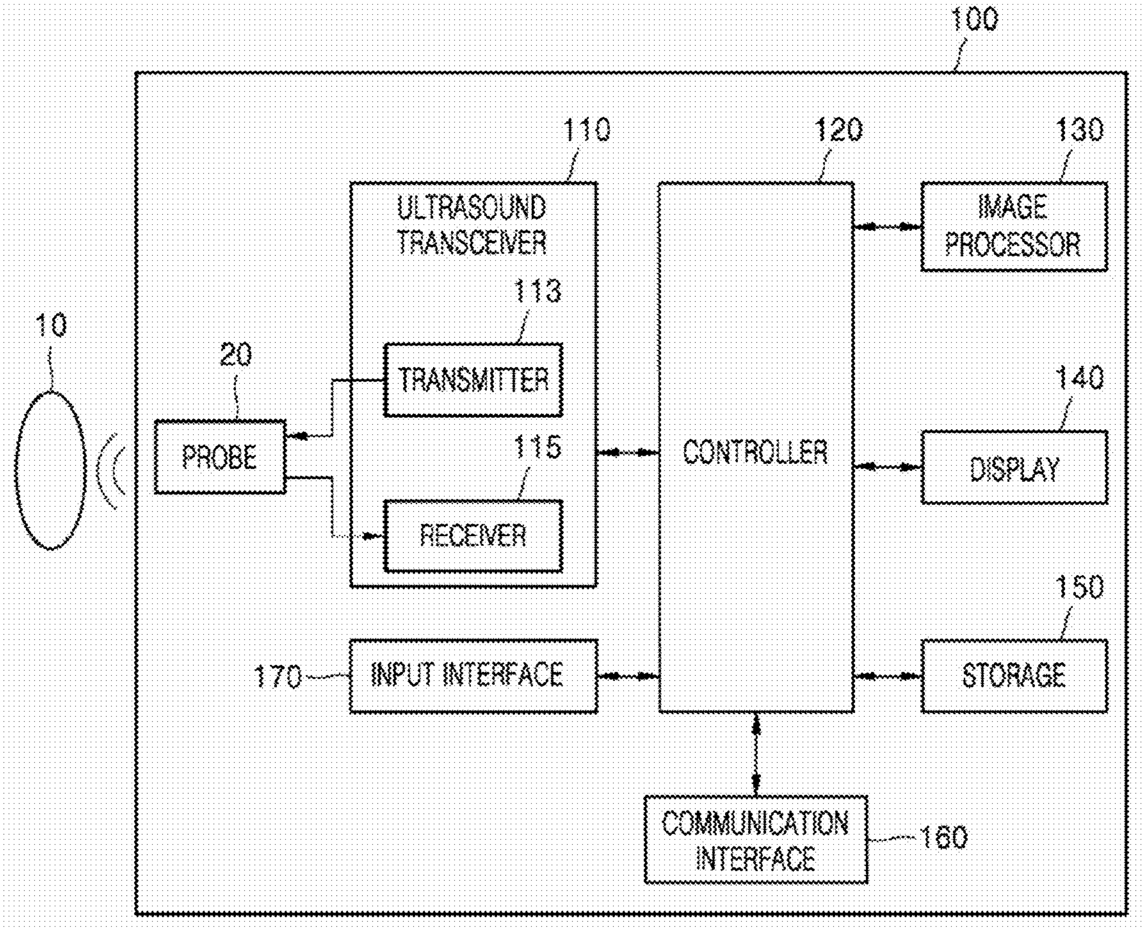
FIG. 1 is a block diagram of a configuration of an ultrasonic imaging apparatus according to an embodiment.

FIG. 1 is a block diagram of a configuration of an ultrasonic imaging apparatus 100 according to an embodiment.

Referring to FIG. 1, the ultrasonic imaging apparatus 100 may include a probe 20, an ultrasound transceiver 110, a controller 120, an image processor 130, a display 140, a storage 150, a communication interface 160, and an input interface 170.

The ultrasonic imaging apparatus 100 may be implemented not only as a cart-type ultrasonic imaging apparatus but also as a portable ultrasonic imaging apparatus.

Examples of the portable ultrasonic imaging apparatus 100 may include, but are not limited to, a smartphone, a laptop computer, a personal digital assistant (PDA), and a tablet personal computer (PC), each of which includes a probe and an application.

The probe 20 may include a plurality of transducers.

The plurality of transducers may transmit ultrasound signals to an object 10 in response to transmission signals applied from a transmitter 113.

The plurality of transducers may receive ultrasound signals reflected from the object 10 to generate reception signals.

In addition, the probe 20 may be formed integrally with the ultrasonic imaging apparatus 100, or may be implemented as a separate part connected to the ultrasonic imaging apparatus 100 in a wired or wireless manner.

In addition, the ultrasonic imaging apparatus 100 may include one or a plurality of probes 20 according to its implemented configuration.

The controller 120 controls the transmitter 113 to generate transmission signals to be respectively applied to the plurality of transducers based on positions and a focal point of the plurality of transducers included in the probe 20.

The controller 120 controls a receiver 115 to generate ultrasound data by performing analog-to-digital conversion (ADC) on the reception signals provided by the probe 20 and summing the digital reception signals based on positions and a focal point of the plurality of transducers.

The image processor 130 generates an ultrasound image by using ultrasound data generated by the receiver 115.

Moreover, the ultrasound image may be displayed not only as a grayscale ultrasound image obtained by scanning the object 10 in an amplitude (A) mode, a brightness (B) mode, and a motion (M) mode, but also as a Doppler image showing a movement of the object 10.

An A mode is the most basic form of ultrasound image display method in which the intensity of a reflected sound is displayed as amplitude on a time (distance) axis, and this mode is advantageous for measuring a distance because amplitude is high for a strong reflected sound and is low for a weak reflected sound, but is currently rarely used because an image changes even when a probe is misoriented slightly.

An M mode is a variation of the A mode and is used to display a distance of a moving reflector as a change over time.

In the M mode, a region of interest (ROI) in a two-dimensional (2D) image is designated as an M line to display a change in the region over time, and this mode is mainly used to observe heart valves and may also obtain recordings of fetal heart sounds, but has recently been largely replaced by a Doppler method.

A B mode is a method currently used in most ultrasonic diagnostic equipment and in which reflected sounds are displayed as dots, the brightness of which is proportional to amplitude of the reflected signals and recently provides brightness levels of 256 or more, and the B mode also allows for real-time imaging and display of organ movements.

A mode called a two-dimensional (2D) mode refers to a B mode, and is a most commonly used mode in which a cross-sectional image of an object is displayed in black or white shades on the screen in real time.

In addition, a Doppler mode is generally used to measure blood flow by detecting the flow of red blood cells in a blood vessel by using the principle that a wavelength is shorter when red blood cells moves toward a probe and the wavelength is longer when they move away from the probe, and Doppler modes include color Doppler, pulsed wave (PW) Doppler (PW), continuous wave (CW) Doppler (CW), etc., according to a method of displaying blood flow.

Doppler images may include a blood flow Doppler image showing flow of blood (also referred to as a color Doppler image), a tissue Doppler image showing a movement of tissue, and a spectral Doppler image showing a moving speed of an object as a waveform.

Other display modes include a complex mode wherein images in other modes are displayed together in 2D by simultaneously applying two or three modes to a single image and a three-dimensional (3D) mode that displays a 3D image. In a B-mode processing process, B-mode components are extracted from ultrasound data and processed, and in an image generation process, an ultrasound image representing the signal intensity as brightness may be generated based on the B-mode components extracted in the B-mode processing process.

In a Doppler processing process, Doppler components are extracted from ultrasound data, and in an image generation process, a Doppler image representing the movement of the object 10 as a color or waveform may be generated based on the extracted Doppler components.

In an image generation process, a 2D ultrasound image or a 3D image of the object 10 may be generated, and an elasticity image representing the degree of deformation of the object 10 due to application of pressure may also be generated. Furthermore, various pieces of additional information may be displayed as text or graphics on the ultrasound image. Furthermore, the generated ultrasound image may be stored in a memory.

In a process of measuring an object in an ultrasound image, a measurement tool for measuring the object may be determined, and one of a plurality of measurement tools may be selected based on a user input. For example, a measurement tool selection menu may be provided for selecting one of a plurality of measurement tools, and the measurement tool selection menu may be displayed on a single screen together with the ultrasound image.

Furthermore, the measurement tool selection menu may be displayed on a separate screen from a touch screen where the ultrasound image is displayed. In addition, one of the plurality of measurement tools may be determined based on a user input for selecting one of a plurality of measurement items to be measured.

The measurement items may include, but are not limited to, a length, an area, or an angle.

In response to receiving a user input for selecting one of the measurement items, a predetermined measurement tool corresponding to the selected measurement item may be determined.

The display 140 may display the generated ultrasound image and various pieces of information processed by the ultrasonic imaging apparatus 100. The ultrasonic imaging apparatus 100 may include one or a plurality of displays 140 depending on its implemented configuration.

Furthermore, the display 140 may be implemented as a touch screen in combination with a touch panel.

The controller 120 may control all operations of the ultrasonic imaging apparatus 100 and flow of signals between the internal elements of the ultrasonic imaging apparatus 100.

The controller 120 may include a memory for storing a program or data necessary to perform functions of the ultrasonic imaging apparatus 100 and a processor for processing the program or data.

The controller 120 may also control an operation of the ultrasonic imaging apparatus 100 by receiving a control signal from the input interface 170 or an external device.

The ultrasonic imaging apparatus 100 includes the communication interface 160 via which it may be connected to external devices (e.g., servers, medical devices, and portable devices such as smartphones, tablet PCs, wearable devices, etc.). The communication interface 160 may include at least one component that enables communication with an external device, and may include, for example, at least one of a short-range communication module, a wired communication module, or a wireless communication module.

The communication interface 160 may receive a control signal and data from an external device and transmit the received control signal to the controller 120 such that the controller 120 may control the ultrasonic imaging apparatus 100 in response to the received control signal. Alternatively, the controller 120 may transmit a control signal to an external device via the communication interface 160 to control the external device in response to the control signal from the controller 120. For example, the external device may process data therein in response to a control signal received from the controller 120 via the communication interface 160. A program (artificial intelligence (AI) or the like) for controlling the ultrasonic imaging apparatus 100 may be installed on the external device, and include instructions to perform some or all of the operations of the controller 120. The program may be pre-installed on the external device or may be installed by a user of the external device by downloading the program from a server that provides applications.

The server that provides applications may include a recording medium where the program is stored.

Furthermore, in a system consisting of the server and a client device, the program may include a storage medium of the server or a storage medium of the client device.

Alternatively, in a case where there is a third device (e.g., a smartphone, a tablet PC, a wearable device, etc.) communicatively connected to the server or the client device, a program product may include a storage medium of the third device.

Alternatively, the program may include a software program itself that is transmitted from the server to the client device or the third device or that is transmitted from the third device to the client device.

In this case, one of the server, the client device, and the third device may execute the program to perform methods according to embodiments.

Alternatively, two or more of the server, the client device, and the third device may execute the program to perform the methods according to the embodiments in a distributed manner. For example, the server (e.g., a cloud server, an AI server, or the like) may execute the program stored therein to control the client device communicatively connected to the server to perform the methods according to the embodiments.

The storage 150 may store various pieces of data or programs for driving and controlling the ultrasonic imaging apparatus 100, input and/or output ultrasound data, obtained ultrasound images, etc. The input interface 170 may receive a user input for controlling the ultrasonic imaging apparatus 100.

Figure 2:
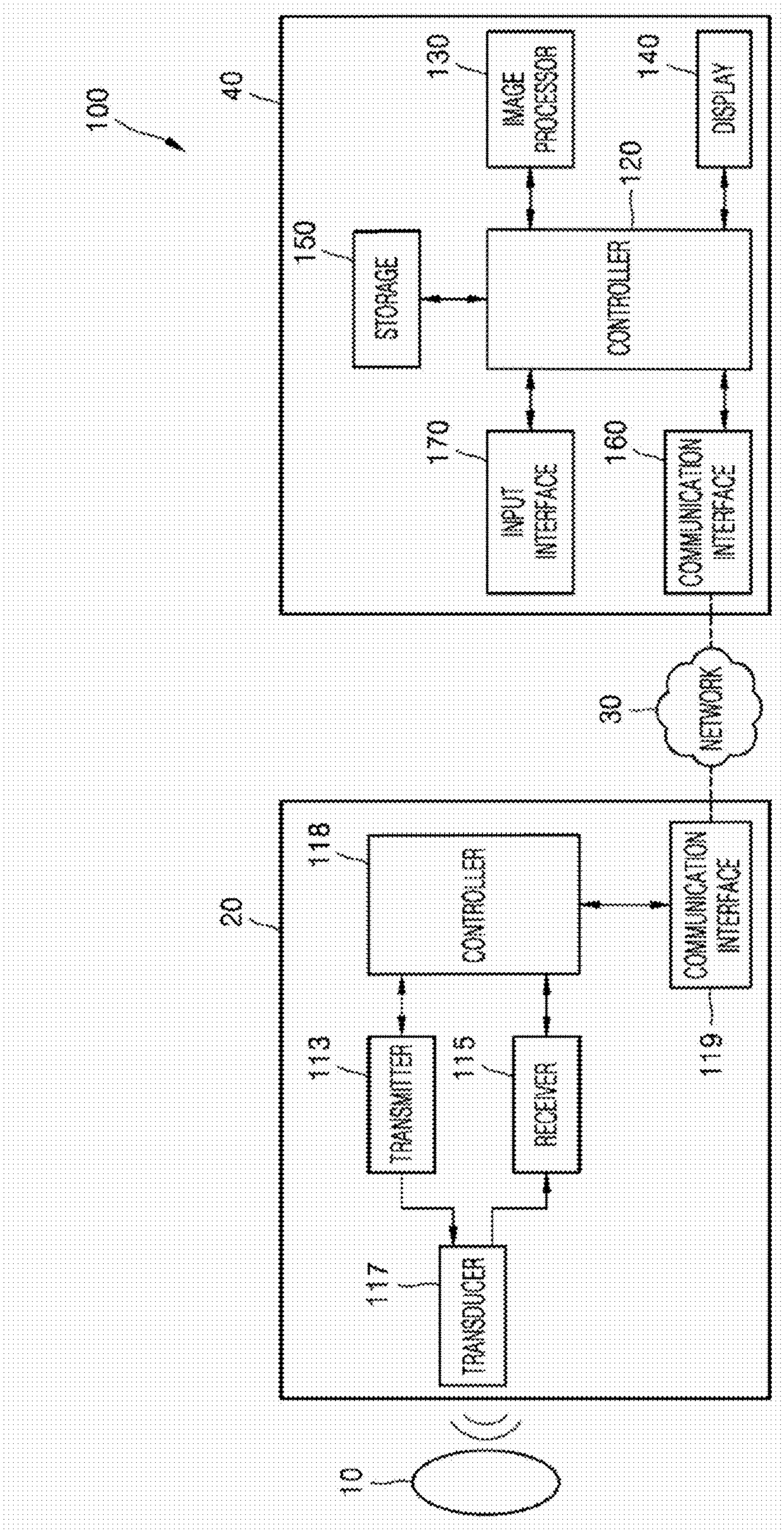
FIG. 2 is a block diagram of a configuration of an ultrasonic imaging apparatus according to an embodiment.

For example, the user input may include, but is not limited to, inputs for manipulating buttons, keypads, mice, trackballs, jog switches, or knobs, an input for touching a touchpad or a touch screen, a voice input, a motion input, and an input of biometric information (e.g., iris recognition, fingerprint recognition, etc.). FIG. 2 is a block diagram of a configuration of an ultrasonic imaging apparatus 100 according to an embodiment.

Referring to FIG. 2, the ultrasonic imaging apparatus 100 may include a wireless probe 20 and an ultrasonic system 40.

The wireless probe 200 may include a transmitter 113, a transducer 117, a receiver 115, a controller 118, and a communication interface 119. Although FIG. 2 shows that the wireless probe 20 includes both the transmitter 113 and the receiver 115, according to its implemented configuration, the wireless probe 20 may include some of the components of the transmitter 113 and the receiver 115 while the ultrasonic system 40 may also include some of them.

Alternatively, the wireless probe 20 may further include an image processor 130. The transducer 117 may include a plurality of transducer elements. The plurality of transducer elements may transmit ultrasound signals to an object 10 in response to transmission signals applied from the transmitter 113.

The plurality of transducer elements may receive ultrasound signals reflected from the object 10 to generate reception signals.

The controller 118 may control the transmitter 113 to generate transmission signals to be respectively applied to the plurality of transducer elements based on positions and a focal point of the plurality of transducer elements. The controller 118 may control the receiver 115 to generate ultrasound data by performing ADC on the reception signals received from the transducer 117 and summing the digital reception signals based on positions and a focal point of the plurality of transducer elements.

Alternatively, when the wireless probe 20 includes the image processor 130, the image processor 130 may generate an ultrasound image based on the generated ultrasound data. The communication interface 119 may wirelessly transmit the generated ultrasound data or ultrasound image to the ultrasonic system 40 via a wireless network.

Alternatively, the communication interface 190 may receive a control signal and data from the ultrasonic system 40.

Furthermore, the ultrasonic imaging apparatus 100 may include one or more wireless probes 20 depending on its implemented configuration. The ultrasonic system 40 may receive ultrasound data or an ultrasound image from the wireless probe 20. The ultrasonic system 40 may include a controller 120, an image processor 130, a display 140, a storage 150, a communication interface 160, and an input interface 170.

The image processor 130 generates an ultrasound image by using the ultrasound data received from the wireless probe 20. The display 140 may display the ultrasound image received from the wireless probe 20, an ultrasound image generated by the ultrasonic system 40, and various pieces of information processed by the ultrasonic imaging apparatus 100. The ultrasonic imaging apparatus 100 may include one or a plurality of displays 140 depending on its implemented configuration.

Furthermore, the display 140 may be implemented as a touch screen in combination with a touch panel.

The controller 120 may control all operations of the ultrasonic imaging apparatus 100 and flow of signals between the internal elements of the ultrasonic imaging apparatus 100.

The controller 120 may include a memory for storing a program or data necessary to perform functions of the ultrasonic imaging apparatus 100 and a processor for processing the program or data.

The controller 120 may also control an operation of the ultrasonic imaging apparatus 100 by receiving a control signal from the input interface 170 or an external device.

The ultrasonic system 40 includes the communication interface 160 via which it may be connected to external devices (e.g., servers, medical devices, and portable devices such as smartphones, tablet personal PCs, wearable devices, etc.)).

The communication interface 160 may include at least one component that enables communication with an external device, and may include, for example, at least one of a short-range communication module, a wired communication module, or a wireless communication module.

The communication interface 160 may receive a control signal and data from an external device and transmit the received control signal to the controller 120 such that the controller 120 may control the ultrasonic imaging apparatus 100 in response to the received control signal. Alternatively, the controller 120 may transmit a control signal to an external device via the communication interface 160 to control the external device in response to the control signal from the controller 120.

For example, the external device may process data therein in response to a control signal received from the controller 120 via the communication interface 160. A program (AI or the like) for controlling the ultrasonic imaging apparatus 100 may be installed on the external device, and include instructions to perform some or all of the operations of the controller 120. The program may be pre-installed on the external device or may be installed by a user of the external device by downloading the program from a server that provides applications.

The server that provides applications may include a recording medium where the program is stored. Furthermore, in a system consisting of the server and a client device, the program may include a storage medium of the server or a storage medium of the client device.

Alternatively, in a case where there is a third device (e.g., a smartphone, a tablet PC, a wearable device, etc.) communicatively connected to the server or the client device, a program product may include a storage medium of the third device.

Alternatively, the program may include a software program itself that is transmitted from the server to the client device or the third device or that is transmitted from the third device to the client device.

In this case, one of the server, the client device, and the third device may execute the program to perform methods according to embodiments. Alternatively, the client device may perform the methods according to the embodiments via the server.

Alternatively, two or more of the server, the client device, and the third device may execute the program to perform the methods according to the embodiments in a distributed manner.

For example, the server (e.g., a cloud server, an AI server, or the like) may execute the program stored therein to control the client device communicatively connected to the server to perform the methods according to the embodiments.

The storage 150 may store various pieces of data or programs for driving and controlling the ultrasonic imaging apparatus 100, input and/or output ultrasound data, ultrasound images, etc. The input interface 170 receives a user input for controlling the ultrasonic imaging apparatus 100. For example, the user input may include, but is not limited to, inputs for manipulating buttons, keypads, mice, trackballs, jog switches, or knobs, inputs for touching a touchpad or a touch screen, a voice input, a motion input, and an input of biometric information (e.g., iris recognition, fingerprint recognition, etc.).

Figure 3:
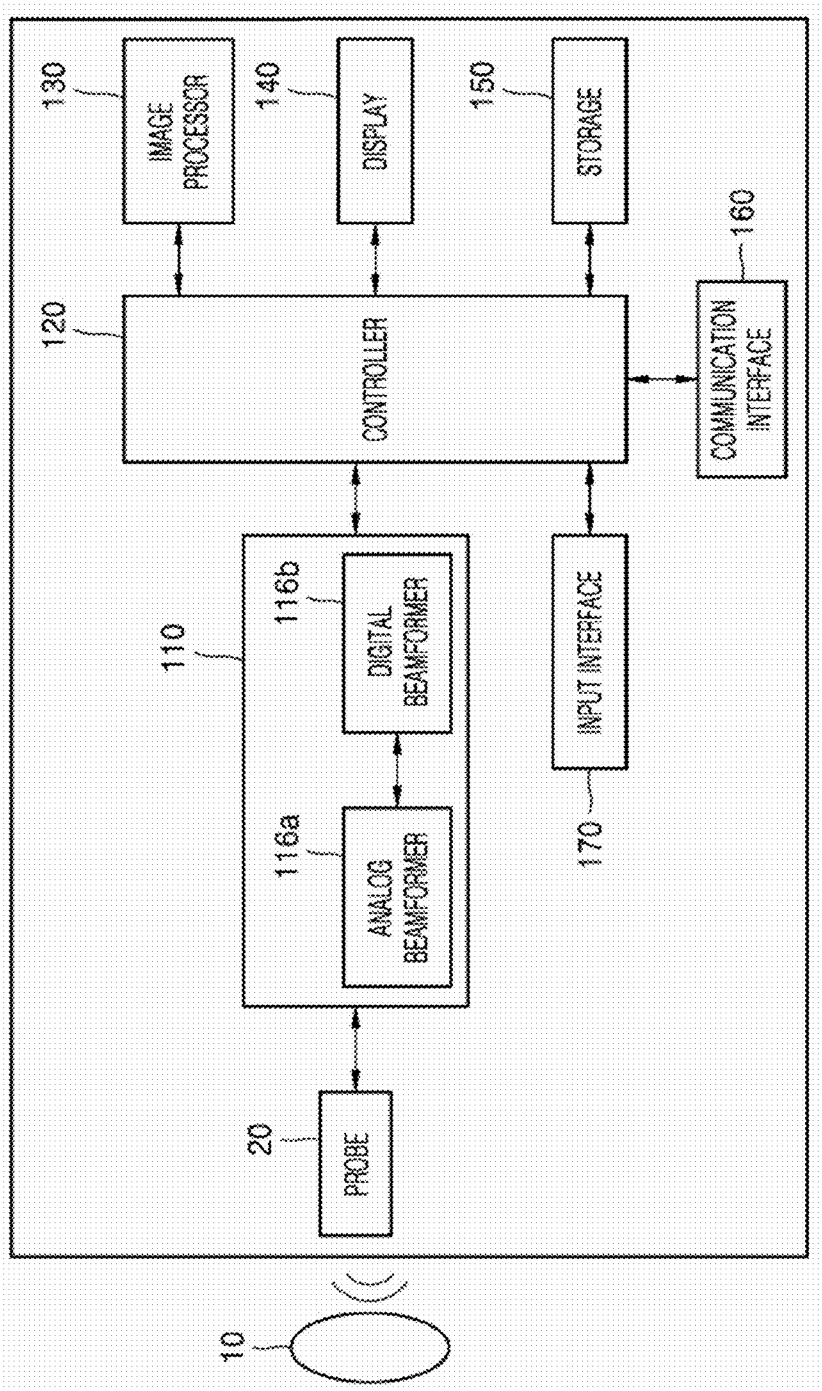
FIG. 3 is a block diagram of a configuration of an ultrasonic imaging apparatus according to an embodiment.

FIG. 3 is a block diagram of a configuration of an ultrasonic imaging apparatus 100 according to an embodiment. Referring to FIG. 3, the ultrasonic imaging apparatus 100 may include a probe 20, an ultrasound transceiver 110, a controller 120, an image processor 130, a display 140, an input interface 170, a storage 150, and a communication interface 160. The probe 20 according to a first embodiment may include a plurality of transducers.

The transducers are arranged in 2D, forming a 2D transducer array.

For example, the 2D transducer array may include a plurality of sub-arrays, each of the plurality of sub-arrays including a plurality of transducers arranged in a first direction, wherein the plurality of sub-arrays are arranged in a second direction that is different from the first direction. Furthermore, the ultrasound transceiver 110 may include an analog beamformer 116*a* and a digital beamformer 116*b*.

Although FIG. 1A illustrates that the ultrasound transceiver 110 and the probe 20 are separate elements, the probe 20 according to the first embodiment may include all or some of the components of the ultrasound transceiver 110 according to its implemented configuration. For example, the probe 20 may include either or both of the analog beamformer 116*a* and the digital beamformer 116*b*.

The controller 120 may calculate a time delay value for digital beamforming with respect to each of the plurality of sub-arrays included in the 2D transducer array.

Also, the controller 120 may calculate a time delay value for analog beamforming for each of the plurality of transducers included in any one of the plurality of sub-arrays. The controller 120 may control the analog beamformer 116*a* and the digital beamformer 116*b* to generate a transmission signal to be applied to each of the plurality of transducers according to the time delay values for analog beamforming and digital beamforming.

The controller 120 may also control the analog beamformer 116*a* to add signals received from the plurality of transducers for each sub-array according to time delay values for analog beamforming.

Furthermore, the controller 120 may control the ultrasound transceiver 110 to perform ADC on the resulting sum signal for each sub-array. In addition, the controller 120 may control the digital beamformer 116*b* to generate ultrasound data by adding the digital output signals according to time delay values for digital beamforming. The image processor 130 generates an ultrasound image by using the generated ultrasound data.

The display 140 may display the generated ultrasound image and various pieces of information processed by the ultrasonic imaging apparatus 100. The ultrasonic imaging apparatus 100 may include one or a plurality of displays 140 depending on its implemented configuration. Furthermore, the display 140 may be implemented as a touch screen in combination with a touch panel.

The controller 120 may control all operations of the ultrasonic imaging apparatus 100 and flow of signals between the internal elements of the ultrasonic imaging apparatus 100.

The controller 120 may include a memory for storing a program or data necessary to perform functions of the ultrasonic imaging apparatus 100 and a processor for processing the program or data.

The controller 120 may also control an operation of the ultrasonic imaging apparatus 100 by receiving a control signal from the input interface 170 or an external device.

The ultrasonic imaging apparatus 100 includes the communication interface 160 via which it may be connected to external devices (e.g., servers, medical devices, and portable devices such as smartphones, tablet PCs, wearable devices, etc.).

The communication interface 160 may include at least one component that enables communication with an external device, and may include, for example, at least one of a short-range communication module, a wired communication module, or a wireless communication module.

The communication interface 160 may receive a control signal and data from an external device and transmit the received control signal to the controller 120 so that the controller 120 may control the ultrasonic imaging apparatus 100 in response to the received control signal.

Alternatively, the controller 120 may transmit a control signal to an external device via the communication interface 160 to control the external device in response to the control signal from the controller 120. For example, the external device may process data therein in response to a control signal received from the controller 120 via the communication interface 160.

A program for controlling the ultrasonic imaging apparatus 100 may be installed in the external device, and include instructions to perform some or all of the operations of the controller 120. The program may be pre-installed on the external device or may be installed by a user of the external device by downloading the program from a server that provides applications. The server that provides applications may include a recording medium where the program is stored.

Furthermore, in a system consisting of the server and a client device, the program may include a storage medium of the server or a storage medium of the client device. Alternatively, in a case where there is a third device (e.g., a smartphone, a tablet PC, a wearable device, etc.) communicatively connected to the server or the client device, a program product may include a storage medium of the third device.

Alternatively, the program may include a software program itself that is transmitted from the server to the client device or the third device or that is transmitted from the third device to the client device.

In this case, one of the server, the client device, and the third device may execute the program to perform methods according to embodiments.

Alternatively, two or more of the server, the client device, and the third device may execute the program to perform the methods according to the embodiments in a distributed manner.

For example, the server (e.g., a cloud server, artificial intelligence (AI) server, or the like) may execute the program stored therein to control the client device communicatively connected to the server to perform the methods according to the embodiments. The storage 150 may store various pieces of data or programs for driving and controlling the ultrasonic imaging apparatus 100, input and/or output ultrasound data, ultrasound images, etc.

The input interface 170 may receive a user input for controlling the ultrasonic imaging apparatus 100.

For example, the user input may include, but is not limited to, inputs for manipulating buttons, keypads, mice, trackballs, jog switches, or knobs, an input for touching a touchpad or a touch screen, a voice input, a motion input, and an input of biometric information (e.g., iris recognition, fingerprint recognition, etc.).

(a) to (c) of FIG. 4 are perspective views of ultrasonic imaging apparatuses 200*a*, 200*b*, and 200*c* according to at least one embodiment. Referring to (a) and (b) of FIG. 4, the ultrasonic imaging apparatuses 200*a* and 200*b* may each include a main display 221 and a sub-display 222.

One of the main display 221 and the sub-display 222 may be implemented as a touch screen.

The main display 221 and the sub-display 222 may display ultrasound images or various pieces of information processed by each of the ultrasonic imaging apparatuses 200*a* and 200*b*. Furthermore, the main display 221 and the sub-display 222 may be implemented as touch screens, and provide a graphical user interface (GUI), thereby receiving, from a user, data for controlling each of the ultrasonic imaging apparatuses 200*a* and 200*b*.

For example, the main display 221 may display an ultrasound image, and the sub-display 222 may display a control panel for controlling display of the ultrasound image in the form of a GUI.

The sub-display 222 may receive data for controlling the display of an image through the control panel displayed in the form of the GUI. Each of the ultrasonic imaging apparatuses 200*a* and 200*b* may control the display of the ultrasound image on the main display 221 by using the input control data.

Referring to (b) of FIG. 4, the ultrasonic imaging apparatus 200*b* may further include a control panel 265 in addition to the main display 221 and the sub-display 222.

The control panel 265 may include buttons, trackballs, jog switches, knobs, etc., and may receive data for controlling the ultrasonic imaging apparatus 200*b* from the user. For example, the control panel 265 may include a time gain compensation (TGC) button 271 and a freeze button 272. The TGC button 271 is for setting a TGC value for each depth of an ultrasound image.

Also, when an input of the freeze button 272 is detected during scanning of an ultrasound image, the ultrasonic imaging apparatus 200*b* may maintain a state in which a frame image at a corresponding time point is displayed.

Moreover, the buttons, trackballs, jog switches, knobs, etc. included in the control panel 265 may be provided as a GUI on the main display 221 or the sub-display 222. Referring to (c) of FIG. 4, an ultrasonic imaging apparatus 200*c* may also be implemented in a portable form. Examples of the ultrasonic imaging apparatus 200*c* that is portable may include, but are not limited to, a smartphone, a laptop computer, a PDA, and a tablet PC, each of which includes a probe and an application.

The ultrasonic imaging apparatus 200*c* may include a probe 20 and a main body 240, and the probe 20 may be connected to one side of the main body 240 in a wired or wireless manner. The main body 240 may include a touch screen 245. The touch screen 245 may display an ultrasound image, various pieces of information processed by the ultrasonic imaging apparatus 200*c*, a GUI, etc.

(a) to (c) of FIG. 5 are perspective views of an ultrasonic imaging apparatus 500 according to at least one embodiment.

Referring to (a) of FIG. 5, an ultrasonic imaging apparatus used indoors or an indoor ultrasonic imaging apparatus 500 generally refers to a non-portable ultrasonic imaging apparatus used for ultrasound diagnosis, and the indoor ultrasonic imaging apparatus 500 is also referred to as cart-based equipment.

The ultrasonic imaging apparatus 500 does not necessarily have to be used only indoors, but for convenience, it will be referred to as the indoor ultrasonic imaging apparatus 500.

The indoor ultrasonic imaging apparatus 500 may have a portable docking unit 580 connected to a portable ultrasonic imaging apparatus 400, and all components of the indoor ultrasonic imaging apparatus 500 used in the disclosure, except for the portable docking unit 580, are commonly used and will not be described in detail.

Unlike the portable ultrasonic imaging apparatus 400, the indoor ultrasonic imaging apparatus 500 has fewer constraints in terms of size, weight, power consumption, etc., so may be developed to offer various diagnostic test items and high performance.

When the portable ultrasonic imaging apparatus 400 is mounted to the indoor ultrasonic imaging apparatus 500, the portable ultrasonic imaging apparatus 400 may provide high performance.

However, a location where the portable ultrasonic imaging apparatus 400 is mounted to the indoor ultrasonic imaging apparatus 500 may be any location where it is convenient for a user to simultaneously use the portable ultrasonic imaging apparatus 400 and the indoor ultrasonic imaging apparatus 500, and is not limited to that shown in (a) of FIG. 5. Furthermore, the portable ultrasonic imaging apparatus 400 may be connected to the indoor ultrasonic imaging apparatus 500 via a wire or integrated connection.

Referring to (a) and (b) of FIG. 5, the portable ultrasonic imaging apparatus 400 of (a) of FIG. 5 may correspond to a portable ultrasonic imaging apparatus 201 of (b) of FIG. 5. The portable ultrasonic imaging apparatus 201 may be formed integrally with a probe (not shown) including a plurality of transducer elements. In detail, the portable ultrasonic imaging apparatus 400 refers to an apparatus that is connected to the indoor ultrasonic imaging apparatus 500 by using a wireless or wired communication method (including a Universal Serial Bus (USB)) and provides ultrasound images to the user by using received ultrasound image data.

For example, the portable ultrasonic imaging apparatus 400 may be a smart device that downloads and installs an application on a smartphone, etc. In detail, the portable ultrasonic imaging apparatus 400 may be an apparatus that is connected to the indoor ultrasonic imaging apparatus 500 by using a wired or wireless communication method and provides ultrasound images to the user by using received ultrasound image data.

For example, wireless communication methods may include at least one of short-range data communication methods including a 60 gigahertz (GHz) millimeter wave (mmWave) wireless local area network (WLAN).

The wireless communication methods may include Wi-Fi, Bluetooth, ZigBee, Wi-Fi Direct (WFD), Infrared Data Association (IrDA), Bluetooth Low Energy (BLE), near field communication (NFC), wireless broadband Internet (WiBro), World Interoperability for Microwave Access (WiMAX), Shared Wireless Access Protocol (SWAP), Wireless Gigabit Alliance (WiGig), and radio frequency (RF) communication.

(b) of FIG. 5 illustrates an ultrasonic diagnostic system in which the portable ultrasonic imaging apparatus 201 is connected to the cart-based ultrasonic imaging apparatus 500. The cart-based ultrasonic imaging apparatus 500 may be connected to the portable ultrasonic imaging apparatus 201 by using the wireless communication methods described above.

In detail, the portable ultrasonic imaging apparatus 201 may be equipped with at least one wireless communication module (not shown) for performing at least one of the wireless communication methods.

Furthermore, the portable docking unit 580 of the cart-based ultrasonic imaging apparatus 500 may include at least one wireless communication module (not shown) for performing wireless communication with the portable ultrasonic imaging apparatus 201. In this case, the wireless communication module in the cart-based ultrasonic imaging apparatus 500 may be a module for performing communication according to at least one of the wireless communication methods. (c) of FIG. 5 illustrates an ultrasonic diagnostic system in which a portable ultrasonic imaging apparatus 202 is connected to the cart-based ultrasonic imaging apparatus 500. The portable ultrasonic imaging apparatus 202 may be coupled to the probe 301 via a probe port. The portable ultrasonic imaging apparatus 202 may generate an ultrasound image by using an ultrasound image corresponding to ultrasound signals received by the probe 301 and display the ultrasound image on a display. The cart-based ultrasonic imaging apparatus 500 may be connected to the portable ultrasonic imaging apparatus 202 by using the wireless communication methods. The connection via wireless communication between the cart-based ultrasonic imaging apparatus 500 and the portable ultrasonic imaging apparatus 202 corresponds to the connection between the cart-based ultrasonic imaging apparatus 500 and the portable ultrasonic imaging apparatus 201, and thus, a detailed description thereof will be omitted.

Hereinafter, a remote ultrasonic diagnostic system according to a first embodiment that may be applied to at least one of the ultrasonic imaging apparatuses described with reference to FIGS. 1 to 3 is described. FIG. 6 is a perspective view of an ultrasonic imaging apparatus 700 according to a first embodiment, FIG. 7 is an enlarged perspective view illustrating the ultrasonic imaging apparatus 700 according to the first embodiment, FIG. 8A is a perspective view of a first arm 721 or a second arm 722 in the ultrasonic imaging apparatus 700 according to the first embodiment, and FIG. 8B is a perspective view of a first lifting arm 731 or a second lifting arm 732 in the ultrasonic imaging apparatus 700 according to the first embodiment. Referring to FIG. 6, the ultrasonic imaging apparatus 700 according to the first embodiment may include a main body 710, a connecting unit 720, and a control panel 770. The main body 710 may be movable using wheels or other moving units, or may be fixed in a particular position without being moved. The main body 710 may be provided as an independent component that may easily be distinguished or a component that is located on one side of other equipment, is difficult to be separated, but is distinguishable.

The control panel 770 is spaced apart from the main body 710 and is provided at an end of the connecting unit 720, and may be connected to the main body 710 via the connecting unit 720 to allow movement and rotation.

The control panel 770 is provided on a top portion of a second connection frame 742, and the second connection frame 742 is provided on a bottom portion of the control panel 770, and referring to FIG. 7, the second connection frame 742 is connected to a second arm 722 so that the control panel 770 may be movable and rotatable due to the connecting unit 720 including the second arm 722. Because the control panel 770 is only able to rotate about a second shaft 752 relative to the second connection frame 742, when the control panel 770 moves, the second connection frame 742 also moves with the control panel 770.

Therefore, the control panel 770 has the same inclination with respect to the second connection frame 742 even when the control plane 770 is moved or rotated. Thus, the control panel 770 may be moved with the same inclination in a plane that perpendicularly bisects the control panel 770 and the second movement frame 742 simultaneously, and may be rotated while remaining in the same plane as the second connection frame 742. The connecting unit 720 connects the control panel 770 to the main body 710 and may be multi-articulated to allow the control panel 770 to move smoothly and have a long movement distance. Referring to FIG. 7, the connecting unit 720 may include the first arm 721 and the second arm 722, and the first arm 721 and the second arm 722 may be included in each of the first lifting arm 731 and the second lifting arm 732.

The first arm 721 includes four link bars that may form a parallelogram in the same plane, and is provided between a first connection frame 741 and the second arm 722 to connect them to each other and is rotatable and movable relative to the main body 710.

The second arm 722 includes four link bars that form a parallelogram in a plane provided independently of the first arm 721, and is rotatable or movable relative to the first arm 721. The first arm 721 is rotatable about the first shaft 751 relative to the first connection frame 741 while remaining in the same plane, and a height of the first arm 721 may be adjusted by moving the four link bars in the same plane.

Although FIG. 8A illustrates up and down movement of the first arm 721, the up and down movement and operating principle of the second arm 722 are the same as those of the first arm 721, and the first arm 721 and the second arm 722 may each include horizontal bars 725 and vertical bars 726.

The first arm 721 and the second arm 722 may each be provided with two horizontal bars 725 and two vertical bars 726. The two horizontal bars 725 may be parallel to each other. The position of the two horizontal bars 725 may be adjusted while remaining parallel to each other in the same plane. The horizontal bars 725 may be connected to the vertical bars 726 to form a parallelogram, and in order to form the parallelogram, the two horizontal bars 725 may be parallel to each other, and the two vertical bars 726 may also be parallel to each other. The parallelogram formed by the horizontal bars 725 and the vertical bars 726 in the first arm 721 is located in the same plane, and arm shafts 724 may be provided at respective corners of the parallelogram. The arm shafts 724 may be provided on the vertical bars 726 so that the horizontal bars 725 and the vertical bars 726 may rotate relative to each other, thereby allowing the control panel 770 to move up and down.

Because two arm shafts 724 are provided for each of the vertical bars 726, the first arm 721 and the second arm 722 each include four arm shafts 724, the first lifting arm 731 and the second lifting arm 732 each include four arm shafts 724, and the connecting unit 720 may include 16 arm shafts 724.

The arm shafts 724 are located to be offset from each other in the vertical bar 726 so that the horizontal bars 725 may move up and down while remaining parallel to each other, and the first arm 721 and the second arm 722 may each form a parallelogram in the same plane. Referring to FIG. 8A, in the first arm 721, the vertical bar 726 connected to the first shaft 751 is fixed, and the vertical bar 726 connected to the third shaft 753 is movable up and down. The arm shafts 724 provided on the vertical bar 726 connected to the first shaft 751 may cause the horizontal bars 725 to rotate while remaining parallel, thereby raising the vertical bar 726 connected to the third shaft 753 and accordingly raising the second arm 722 and the control panel 770.

Referring to FIG. 8A, each gas spring is provided between two vertical bars 726 in the first arm 721, and both ends of the gas spring are respectively connected to the arm shafts 724 to compensate for weight when the first arm 721 moves up and down. When the gas spring is a locking gas spring 723, the gas springs may perform the function of fixing up and down positions of the first arm 721 in addition to weight compensation.

The gas spring is provided diagonally between the vertical bars 726, and may compensate for weight. One end of the gas spring is connected to the lower arm shaft 724 in the vertical bar 726 connected to the first shaft 751 and another end thereof is connected to the upper arm shaft 724 in the vertical bar 726 connected to the third shaft 753. The gas springs may include a normal gas spring for compensating for weight and a locking gas spring 723 that acts as a brake by fixing the up and down positions in addition to compensating for weight, and the gas springs may include at least one locking gas spring 723. However, when three or four locking gas springs 723 are provided, a large amount of force is required to manipulate the connecting unit 720, which may reduce manipulation performance.

In FIG. 8A, the first arm 721 may be raised up to 140 mm, and thus, the first lifting arm 731 including the first arm 721 and the second arm 722 may move up and down to a maximum height of 280 mm.

Referring to FIG. 8B, the first arm 721 and the second arm 722 provided in a pair may be included in each of the first lifting arm 731 and the second lifting arm 732. Because the gas springs 723 are respectively provided in the first arm 721 and the second arm 722, the two gas springs may be provided for each of the first lifting arm 731 and the second lifting arm 732. Whether a locking gas spring 723 is operated is determined by a brake wire 760, and in order for the locking gas spring 723 to prevent up and down movement of the first lifting arm 731 or the second lifting arm 732, the two locking gas springs 723 need to be arranged in a line.

On the other hand, when one of the locking gas springs 723 is located in the first lifting arm 731 and the other is located in the second lifting arm 732, this is equivalent to arranging the locking gas springs 723 diagonally opposite to each other or parallel to each other, so that the normal gas spring and the locking gas spring 723 are arranged in a line on each of the first lifting arm 731 and the second lifting arm 732.

In this case, because the normal gas spring may compensate for weight but not function as a brake, up and down positions of each of the first lifting arm 731 and the second lifting arm 732 need to be fixed via one locking gas spring 723. Because each of the first lifting arm 731 and the second lifting arm 732 includes the first arm 721 and the second arm 722, the locking gas springs 723 are respectively arranged in the first arm 721 and the second arm 722, e.g., by providing one locking gas spring 723 in the first arm 721 of the first lifting arm 731 and the other locking gas spring 723 in the second arm 722 of the second lifting arm 732 so that the locking gas springs 723 are arranged diagonally opposite to each other.

When the locking gas springs 723 are provided diagonally opposite to each other, locations to fix the up and down positions of the control panel 770 and support a force are provided diagonally from each other, and thus, twisting may occur and an unstable structure may be created. Accordingly, the two locking gas springs 723 need to be arranged in a line in the first lifting arm 731 or the second lifting arm 732. The two locking gas springs 723 are arranged in a line in the first lifting arm 731 or the second lifting arm 732, and the remaining two normal gas springs are provided in the first lifting arm 731 or the second lifting arm 732 where the locking gas springs 723 are not arranged, so that at least one of the first lifting arm 731 or the second lifting arm 732 may operate as a brake to prevent up and down movement.

Referring to FIG. 8B, as the connecting unit 720 moves left and right, the control panel 770 may move forward and backward. In detail, the first arm 721 rotates about the first shaft 751, and the second arm 722 rotates about the third shaft 753 relative to the first arm 721, and the second arm 722 rotates about the second shaft 752, thereby allowing the control panel 770 to move forward and backward. Therefore, the connecting unit 720 including the first arm 721 and the second arm 722 is provided as a multi-articulated arm, thereby achieving a longer radius of movement and a smooth movement. Referring to FIG. 7, because the first arm 721 is connected to the first connection frame 741 and is rotatable about the first shaft 751, the second arm 722 is connected to the second connection frame 742 and is rotatable about the second shaft 752, and the second arm 722 is rotatable about the third shaft 753, the first lifting arm 731 including the first arm 721 and the second arm 722 may rotate in the three places, and similarly, the second lifting arm 732 may also rotate in three places.

When a plane perpendicular to the first shaft 751 is referred to as a first plane, a plane perpendicular to the second shaft 752 is referred to as a second plane, and a plane perpendicular to the third shaft 753 is referred to as a third plane in the first lifting arm 731 and the second lifting arm 732, the first to third planes may be parallel even when the control panel 770 is rotated or moved.

Because an inclination of the first shaft 751, the second shaft 752, and the third shaft 753 does not change when the control panel 770 is rotated or moved, the first shaft 751, the second shaft 752, and the third shaft 753 may be arranged parallel to one another, and accordingly, an inclination of the control panel 770 connected to the second connection frame 742 in which the second shaft 752 is provided may be maintained when the control panel is rotated (when moved in a plane) so that the control panel 770 moves with a constant inclination.

An inclination of the vertical bars 726 of the first arm 721 and the second arm 722 connected to the first shaft 751, the second shaft 752, and the third shaft 753 does not change even when the control panel 770 is rotated or moved, and thus, the vertical bars 726 may remain parallel to each other.

In the ultrasonic imaging apparatus 700 according to the first embodiment, because the inclination of the control panel 770 does not change even when the control panel 770 is rotated or moved, the user may easily use it by simply adjusting the position of the control panel 770. FIG. 9 is a diagram illustrating a process in which brakes 754 are operated in the ultrasonic imaging apparatus 700 according to the first embodiment, FIG. 10A is a diagram illustrating a process in which the brake wire 760 is operated in the ultrasonic imaging apparatus 700 according to the first embodiment, and FIG. 10B is a diagram illustrating a process in which the brake wire 760 is operated in the ultrasonic imaging apparatus 700 according to the first embodiment.

Referring to FIGS. 9, 10A, and 10B, the brakes 754 are shown that act on the first shaft 751 and the second shaft 752 to prevent rotation thereof, and the brakes 754 may be provided in the first connection frame 741 where the first shaft 751 is provided and the second connection frame 742 where the second shaft 752 is provided.

The brake 754 may include a band (with no reference number shown) surrounding a circumference of the first shaft 751 or the second shaft 752. Normally (or at a default position), the band may be pulled to one side to contact the circumference of the first shaft 751 or the second shaft 752, thereby hindering rotation of the first arm 721 and the second arm 722 and thus fixing the position of the control panel 770.

The brake 754 may be an electronic device operated by an electrical signal, and may be operated by manual manipulation or by an electric button that replaces the manual manipulation.

In the brake 754, the band is pulled by the brake wire 760 to hinder rotation of the first arm 721 and the second arm 722. When the brake wire 760 does not operate, the band is loosely provided so that the first arm 721 and the second arm 722 may rotate, allowing the control panel 770 to rotate and move.

The band of the brake 754 may be provided as high-friction rubber or the like, or when the first shaft 751 or the second shaft 752 has a sawtooth shape, a structure having friction may be used, which has a shape that allows engagement with the sawtooth-shaped shaft to prevent rotation thereof. Referring to FIG. 10A, the first connection frame 741 or the second connection frame 742 is shown, and for convenience, descriptions will be provided with respect to the first connection frame 741.

The first connection frame 741 is provided with two first shafts 751, and the first shafts 751 are respectively connected to the first arms 721 to rotate the first arms 721.

The brake wire 760 is connected to the brake 754 provided on the first shaft 751 such that operation of the brake wire 760 may hinder the rotation of the first shaft 751 and accordingly suppress the rotation of the first arm 721.

Referring to FIG. 10A, when the brake wire 760 is pulled in the direction of the first connection frame 741, or a member connected to the structure having friction or the band of the brake 754 may slide diagonally relative to the brake wire 760 to pull the band of the brake 754 connected to the first shaft 751, thereby hindering the rotation of the first shaft 751 and thus preventing the rotation of the first arm 721.

The brakes 754 are respectively separately provided on the first shafts 751, but are interlocked with the brake wire 760 so that an operation of the brake wire 760 may cause the two brakes 754 provided in the first connection frame 741 to operate. In addition, the brake wire 760 is connected to the locking gas springs 723 provided in the first lifting arm 731 or the second lifting arm 732, so when the brake wire 760 is pulled in the direction of the first connection frame 741, the operation of the locking gas spring 723 may be stopped, thereby preventing the control panel 770 from moving up and down.

Because the brake wire 760 is connected to the locking gas springs 723 and the brakes 754, when the brake wire 760 is pulled toward the first connection frame 741 as shown in FIG. 10A, the operation of the locking gas springs 723 is stopped to prevent the up and down movement of the control panel 770 while the rotation of the first shaft 751 is hindered by the brake 754 to prevent the rotation of the control panel 770. Accordingly, the position of the control panel 770 may be fixed due to the operation of the brake wire 760.

Referring to FIG. 10B, when the brake wire 760 moves away from the first connection frame 741, the band of the brake 754 or the member connected to the structure having friction slides diagonally relative to the brake wire 760 to loosen the band of the brake 754 connected to the first shaft 751 or separate the structure having friction from the first shaft 751, thereby allowing rotation of the first shaft 751 and accordingly rotation of the first arm 721. When the operation of the brake wire 760 is released by moving away from the first connection frame 741, the locking gas springs 723 are operated to allow up and down movement of the control panel 770, and the brakes 754 do not hinder the rotation of the first shaft 751 to enable rotation of the control panel 770.

Because the brake wire 760 is also operated in the second connection frame 742 similarly as in the first connection frame 741, when the brake wire 760 is operated by being pulled toward the second connection frame 742, the band of the brake 754 hinders the rotation of the second shaft 752, thereby preventing the movement of the control panel 770, and when the operation of the brake wire 760 is released by moving away from the second connection frame 742, the band of the brake 754 is loosened to allow the second shaft 752 to rotate, thereby allowing the control panel 770 to move.

In the ultrasonic imaging apparatus 700 according to the first embodiment, at least two locking gas springs 723 are provided to prevent up and down movement, and a total of four brakes 754 for preventing rotational movement are provided, including two on each of the first connection frame 741 and the second connection frame 742, so that the position of the control panel 770 may be securely fixed when the brake wire 760 is operated.

In addition, even when the brake 754 is operated first by an electric signal, manual manipulation, or electric button before the brake wire 760 is operated, the brake wire 760 is operated accordingly to stop the operation of the locking gas spring 723, thereby stopping the movement and rotation of the connecting unit 720 and fixing the position of the control panel 770.

FIG. 11A is a diagram illustrating movement of the connecting unit 720 for moving the control panel 770 up and down in the ultrasonic imaging apparatus 700 according to the first embodiment, FIG. 11B is a diagram illustrating the movement of the connecting unit 720 for moving the control panel 770 up and down in the ultrasonic imaging apparatus 700 according to the first embodiment, and FIG. 11C is a diagram illustrating the movement of the connecting unit 720 for moving the control panel 770 up and down in the ultrasonic imaging apparatus 700 according to the first embodiment.

Referring to FIG. 11A, the first lifting arm 731 and the second lifting arm 732 are provided at the same height, so that the first arm 721, the second arm 722, and the third shaft 753 are provided at the same height, and a second connection frame 742 is located at the top and a first connection frame 741 is located at the bottom.

As shown in FIG. 11A, the brake wire 760 may be operated to stop the operation of the locking gas springs 723 and operate the brake 754 to fix the position of the control panel 770 provided on the top of the second connection frame 742.

When the first lifting arm 731 and the second lifting arm 732 move up and down, the horizontal bars 725 and the vertical bars 726 in the first arm 721 and the second arm 722 may form a parallelogram in the same plane and move up and down to stably adjust a height of the control panel 770.

Referring to FIG. 11B, the operation of the brake wire 760 is released to allow the first arm 721 and the second arm 722 to move, but the first arm 721 is fixed at the same position as shown in FIG. 11A while the second connection frame 742 and the second arm 722 is moved up and down.

Although the vertical bar 726 connected to the third shaft 753 in the second arm 722 is fixed at the same position, the horizontal bars 725 rotate and rise while remaining parallel due to the arm shafts 724 provided on the vertical bar 726, and thus, when the control panel is moved up and down, up and down movement of the second arm 722, which is located closer to the control panel 770, occurs first. When the horizontal bars 725 of the second arm 722 rises to a maximum height and the height of the control panel 770 is no longer changed by the second arm 722, the horizontal bars 725 in the first arm 721 may rotate about the arm shafts 724 provided on the vertical bars 726 to change the height of the control panel 770.

Referring to FIG. 11C, after the horizontal bars 725 of the second arm 722 rise to a maximum height, the first arm 721 begins to rise, so that for the up and down movement of the control panel 770, the second arm 722 may move first and then the first arm 721 may move, and depending on the force applied, the first arm 721 and the second arm 722 may move simultaneously.

As shown in FIGS. 11A to 11C, the control panel 770 and the second connection frame 742 provided on the bottom of the control panel 770 are raised by raising the first arm 721 and the second arm 722, and because the lifting arms 731 and 732 are not twisted during the raising process, the first shaft 751, the second shaft 752, and the third shaft 753 remain parallel to one another, and the first plane, which is a plane perpendicular to the first shaft 751 in the first connection frame 741, and the second plane, which is a plane perpendicular to the second shaft 752 in the second connection frame 742, remain parallel to each other.

During the raising process, the third plane perpendicular to the third shaft 753 remains parallel to the first and second planes, and thus, in the ultrasonic imaging apparatus 700 according to the first embodiment, the control panel 770 may change its position while remaining parallel to the main body 710 or the first connection frame 741.

In FIGS. 11A to 11C, the first shaft 751 and the second shaft 752 are prevented from rotating by the brakes 754, and the third shaft 753 located between the first arm 721 and the second arm 722 is not provided with a brake 754 but is not able to rotate because the rotation of the first shaft 751 and the second shaft 752 is prevented. The third shaft is actually be prevented from rotating.

FIG. 12A is a diagram illustrating movement of the connecting unit 720 for moving the control panel 770 forward and backward and left and right in the ultrasonic imaging apparatus 700 according to the first embodiment, FIG. 12B is a diagram illustrating the movement of the connecting unit 720 for moving the control panel 770 forward and backward and left and right in the ultrasonic imaging apparatus 700 according to the first embodiment, FIG. 12C is a diagram illustrating the movement of the connecting unit 720 for moving the control panel 770 forward and backward and left and right in the ultrasonic imaging apparatus 700 according to the first embodiment, and FIG. 12D is a diagram illustrating the movement of the connecting unit 720 for moving the control panel 770 forward and backward and left and right in the ultrasonic imaging apparatus 700 according to the first embodiment.

FIGS. 12A to 12D illustrate a process by which the connecting unit 720 for moving the control panel 770 is moved forward and backward and left and right, and the connecting unit 720 may be moved forward and backward and left and right by rotating the first arm 721 and the second arm 722 about the first shaft 751, second shaft 752, and third shaft 753.

Compared to in FIG. 12A, in FIG. 12B, by rotating the first arm 721 and the second arm 722 about the first shaft 751, second shaft 752, and third shaft 753, the connecting unit 720 may be moved forward and backward by reducing a gap between the second connection frame 742 and the first connection frame 741.

In FIGS. 12C and 12D, by moving the second connection frame 742 left and right to shift it to one side, the two first arms 721 form an angle of 90 degrees therebetween, the first shaft 751, the second shaft 752, and the third shaft 753 are arranged parallel to one another, and the first to third planes are also arranged parallel to one another. Thus, the position of the control panel 770 is changed while the control panel 770 a specific inclination of the control panel 770 is maintained, thereby eliminating the need to adjust the inclination.

When the user releases the operation of the brake wire 760 and applies a force to the control panel 770 when moving the control panel 770, the second arm 722, which is closer to the control panel 770, may receive the force first to move, and the first arm 721 may move with the second arm 722 when the control panel 770 is outside a radius of movement of the second arm 722 or a strong force is applied to the control panel 770.

In FIG. 12C or FIG. 12D, the connecting unit 720 is multi-articulated to allow the first arm 721 and the second arm 722 to rotate about the first shaft 751, the second shaft 752, and the third shaft 753 so that the control panel 770 may be located further away from the first connection frame 741 or the main body 710.

In FIG. 12B, forward and backward movement is possible up to 300 mm, and in FIGS. 12C and 12D, left and right movement is possible up to 550 mm, so the ultrasonic imaging apparatus 700 according to the first embodiment may have a larger radius of movement for the left and right movement than for forward and backward movement.

FIG. 13A is a diagram illustrating movement of the connecting unit 720 for diagonally moving the control panel 770 in the ultrasonic imaging apparatus 100 according to the first embodiment, and FIG. 13B is a diagram illustrating the movement of the connecting unit 720 for diagonally moving the control panel 770 in the ultrasonic imaging apparatus 700 according to the first embodiment.

The ultrasonic imaging apparatus 700 according to the first embodiment may perform up and down movement and left and right movement separately, and also perform a diagonal movement in which the up and down movement and the left and right movement proceed simultaneously, thereby enabling 3D movement of the control panel 770.

In FIG. 13A, as the horizontal bars 725 of the first arm 721 and the horizontal bars 725 of the second arm 722 are lowered while remaining parallel, the vertical bars 726 of the first arm 721 and the vertical bars 726 of the second arm 722 are also lowered, the first arm 721 rotates about the first shaft 751 provided in the first connection frame 741, the second arm 722 rotates about the second shaft 752 provided in the second connection frame 742, and the second arm 722 rotates about the third shaft 753 relative to the first arm 721, thereby enabling a diagonal movement of the second connection frame 742 of the connecting unit 720 as shown in FIG. 13B.

In the ultrasonic imaging apparatus 700 according to the first embodiment, the connecting unit 720 may be moved diagonally to various positions within a radius of movement of the first arm 721 and the second arm 722, and the operation of the brake wire 760 always needs to be released before movement of the connecting unit 720.

The brake wire 760 is connected to the locking gas springs 723 and the brakes 754, and may be operated by pulling it as shown in FIGS. 10A and 10B. The brake wire 760 may be pulled by an actuator 851. The actuator 851 may be operated by an electric button 171 (or operation button) and then whether the brake wire 760 is to be operated may be determined by clicking the electric button 171.

The user may move the control panel 770 by clicking the electric button 171 and applying force, and the electric button 171 may use at least two methods for accomplishing this.

The electric button 171 may use an on/off method of fixing the position of the control panel 770 by clicking the electric button to move the control panel 770 and then clicking again to operate the brake wire 760, or a method of moving the control panel 770 by continuously clicking the electric button 171.

The electric button 171 may cause the brake wire 760 to operate for some of the four brakes 754 and the at least two locking gas springs 723 connected to the brake wire 760, thereby limiting the form of movement of the control panel 770. For example, when the electric button 171 causes the brake wire 760 to operate for all the four brakes 754, the control panel 770 may not be able to rotate but only move up and down.

When the electric button 171 causes the brake wire 760 to operate only for the two brakes 754 provided in the first connection frame 741, rotation about the first shaft 751 may not be possible, but rotation about the second shaft 752 may be possible.

When the electric button 171 causes the brake wire 760 to operate for the locking gas springs 723, the control panel 770 is not able to be moved up and down and may only be rotated to move in a plane at the same height.

Even when the operation of the brake wire 760 is released by clicking the electric button, the connecting unit 720 may support the control panel 770 not to move without the user applying additional force, thereby preventing the control panel 770 from moving only by clicking the electric button 171.

FIG. 14 is a diagram illustrating the connection of a second shaft 752 in an ultrasonic imaging apparatus 700 according to a second embodiment, FIG. 15 is a diagram illustrating the connection of the second shaft 752 in the ultrasonic imaging apparatus 700 according to the second embodiment, and FIG. 16 is a diagram illustrating movement of a connecting unit 720 for diagonally moving a control panel 770 in the ultrasonic imaging apparatus 700 according to the second embodiment.

Referring to FIG. 14, a first rotating member 781 connected to the second shaft 752 or a second rotating member 782 not connected to the second shaft 752 may be respectively provided at ends of second arms 722.

Because the first rotating member 781 is connected to the second shaft 752, and the second shaft 752 is connected to a second connection frame 742 provided on the bottom of the control panel 770, the first rotating member 781 is directly connected to the control panel 770.

The second rotating member 782, which is not connected to the second shaft 752, may be connected to the first rotating member 781, an intermediate member, or a separate control panel.

When the second rotating member 782 is connected to the first rotating member 781, the second rotating member 782 may support a bottom of the first rotating member 781 and be connected to the first rotating member 781 obliquely with respect to the second shaft 752, so the second rotating member 782 may not be directly connected to the control panel 770.

When the control panel 770 is supported only by the first rotating member 781 directly connected to the second shaft 752, shaking may occur and a large load may be placed on the first rotating member 781, and to prevent this, the second rotating member 782 may be connected at the bottom of the first rotating member 781 to distribute the load placed on the first rotating member 781, and move together with the first rotating member 781 to prevent shaking as well.

Referring to FIG. 16, which shows the control panel 770 and the connecting unit 720 when viewed from the bottom, first arms 721 are respectively connected to first shafts 751 in the first connection frame 741, and the first arms 721 are respectively connected to the second arms 722 via third shafts 753, and the first rotating member 781 or the second rotating member 782 are respectively provided at ends of the second arms 722.

The second rotating member 782 is provided at the bottom of the first rotating member 781 to support the load of the first rotating member 781 which is connected to the second shaft 752 to enable movement of the control panel 770, and is connected to the first rotating member 781 with an axis that is offset from the second shaft 752 so that they may move together.

The first shafts 751 of the first connection frame 741 are provided with brakes 754 to control movement of the pair of first arms 721 connected to the first shafts 751, and the second shaft 752 of the second connection frame 742 is also provided with the brake 754 but may only directly control the movement of the second arm 722 provided with the first rotating member 781 and not directly control the movement of the second arm 722 provided with the second rotating member 782.

Because the second rotating member 782 is connected to the first rotating member 781, when the movement of the first rotating member 781 is controlled by the brake 754 provided on the second shaft 752, the movement of the second rotating member 782 may also be indirectly controlled.

Referring to FIGS. 14 and 15, the second shaft 752 is connected to the first rotating member 781, the second rotating member 782 is connected to the first rotating member 781 on an axis that is offset from the second shaft 752, and a cross-sectional area of the first rotating member 781 may be larger than that of the second rotating member 782.

The first rotating member 781 may have a larger cross-sectional area than the second rotating member 782 in order to be connected to the second shaft 752 and connected to the second rotating member 782 at the bottom.

Although FIG. 14 shows that the second rotating member 782 is connected to the first rotating member 781, the second rotating member 782 may be spaced apart from and not connected to the first rotating member 781 but may be connected to an intermediate member (with a reference number not shown) or a separate control panel.

While the first rotating member 781 and the second rotating member 782 may each include different components, the intermediate member or separate control panel that may be connected to the second rotating member 782 is connected to the control panel 770 connected to the first rotating member 781, and consequently, the components of the connecting unit 720 may move together.

The intermediate member or separate control panel that may be provided on the second rotating member 782 may be detachable, so the second rotating member 782 may be selectively coupled to the first rotating member 781, the intermediate member, or the separate control panel.

The intermediate member or the separate control panel may determine whether to connect to the control panel 770 connected to the first rotating member 781, and thus, the intermediate member or the separate control panel may be sequentially connected to the control panel 770 so that they move together, or may be separated therefrom so that each of a first lifting arm 731 and a second lifting arm 732 may move separately.

The intermediate member or the separate control panel may be connected to other components such as the display 140, so when the display 140 is provided in the control panel 770 connected to the first rotating member 781, the ultrasonic imaging apparatus 700 may include a plurality of displays 140.

FIG. 17 is a diagram illustrating the movement of the connecting unit 720 for diagonally moving the control panel 770 in the ultrasonic imaging apparatus 700 according to the second embodiment, and FIG. 18 is a diagram illustrating the movement of the connecting unit 720 for diagonally moving the control panel 770 in the ultrasonic imaging apparatus 700 according to the second embodiment.

The first rotating member 781 connected to the second shaft 752 is coupled to the second rotating member 782 at the bottom and may move together, enabling plane movement of the control panel 770.

While the ultrasonic imaging apparatus 700 according to the first embodiment may have the two second shafts 752 provided in the second connection frame 742 and respectively connected to the ends of the second arms 722, the ultrasonic imaging apparatus 700 according to the second embodiment may have a different range of operation by having one second shaft 752 provided in the second connection frame 742, the first rotating member 781 connected to the second shaft 752, and the second rotating member 782 connected to the first rotating member 781 without being connected to the second shaft 752.

As the second rotating member 782 is not connected to the second shaft 752, the shape of the first lifting arm 731 and the second lifting arm 732 may vary in the connecting unit 720 for supporting the control panel 770 at a specific height.

Referring to FIG. 17, in the first lifting arm 731 provided with the first rotating member 781, the first arm 721 is provided horizontally and the second arm 722 is raised, whereas in the second lifting arm 732 provided with the second rotating member 782, the first arm 721 is raised and the second arm 722 is provided horizontally. Heights to which the first arm 721 and the second arm 722 are raised to set a particular height may vary.

Referring to FIG. 18, because the second arm 722 is raised in the first lifting arm 731 provided with the first rotating member 781, and the first arm 721 is raised in the second lifting arm 732 provided with the second rotating member 782, so that only the first rotating member 781 is connected to the second shaft 752, each of the first lifting arm 731 and the second lifting arm 732 has a different connection point at its end and may be driven independently.

According to another embodiment, the ultrasonic imaging apparatus 700 is provided with a plurality of third shafts 753, each connected to a vertical bar 726 of the first arm 721 and a vertical bar 726 of the second arm 722, so that the first arm 721 and the second arm 722 may each rotate about the third shaft 753.

The third shaft 753 may include a brake 754 provided with a structure having friction located around the third shaft 753 so that the structure around the third shaft 753 contacts the third shaft 753 due to an electrical signal or manual manipulation to prevent the rotation of the first arm 721 or the second arm 722.

When the brake wire 760 is operated, the third shaft is also stopped from rotating along with the first shaft 751 and the second shaft 752, and thus, the operation of the brakes 754 provided on the first shaft 751, the second shaft 752, and the third shaft 753 may be controlled by an operation of the brake wire 760.

According to another embodiment, in the ultrasonic imaging apparatus 700, a locking gas spring 723 may be provided in the first lifting arm 731 or the second lifting arm 732 so that up and down positions may be fixed by one of the first and second lifting arms 731 and 732.

In addition, because the first lifting arm 731 and the second lifting arm 732 are provided asymmetrically due to different lengths of horizontal bars 725, the overall shape may vary, and positions of the third shafts 753 in the first lifting arm 731 and the second lifting arm 732 may be different from each other, which may result in different movements.

As a length of each of the first lifting arm 731 and the second lifting arm 732 varies, up and down positions thereof may be adjusted to a limited degree.

FIG. 19A is a cross-sectional view illustrating an operation of a locking unit 810 in an ultrasonic imaging apparatus 700 according to a 1st-1 embodiment, and FIG. 19B is a cross-sectional view illustrating an operation of the locking unit 810 in the ultrasonic imaging apparatus 700 according to the 1st-1 embodiment.

Each of the ultrasonic imaging apparatuses 700 shown in FIGS. 19A to 23B may include a main body 710, a connecting unit 720 that rotates and moves relative to a first connection frame 741 provided on the main body 710, a control panel 770 provided on an end of the connecting unit 720 to be movable up and down or diagonally while remaining horizontal with respect to the main body 710, and a locking unit 810 that controls movement of the control panel 770.

The locking unit 810 may include a locking gas spring 723 and a brake 754 to simultaneously control the movement of the control panel 770.

The locking gas spring 723 is provided in the connecting unit 720 to control the up and down movement of the control panel 770, and is normally in a locked state to control the movement of the connecting unit 720, but may be unlocked when pulled to thereby enable movement of the connecting unit 720. The brake 754 may be provided in a first connection frame 741 located between the main body 710 and the connecting unit 720 and a second connection frame 742 located between the connecting unit 720 and the control panel 770, and may be operated to control forward and backward and left and right movements of the connecting unit 720, thereby controlling forward and backward and left and right movements of the control panel 770. The locking unit 810 may include a link 830 and a locking device 820 that is operated mechanically or electrically to cause the locking gas spring 723 and the brake 754 to be in a locked state.

The locking device 820 may include a cable 840 that moves the link 830 when operated mechanically, and an actuator 851 and a drive shaft 852 that move the link 830 when operated electrically.

The link 830 may include a rotary link 831 that rotates about one axis due to operation of the locking device 820 and a linear link 832 that moves along a straight line, and the rotary link 831 and the linear link 832 may be connected to each other in a partially overlapping manner, so that when one link 830 is operated, the other link 830 may also be operated.

Because the locking device 820 may be connected to at least one of the rotary link 831 or the linear link 832, by operating the locking device 820, the link 830 may be operated continuously to control the locking gas spring 723 and the brake 754.

FIG. 19A is a cross-sectional view of the locking unit 810 provided in the first connection frame 741 or the second connection frame 742, which illustrates the movement of the locking device 820 and the link 830 included in the locking unit 810.

The locking device 820 may include the cable 840, the actuator 851, and the drive shaft 852 and be operated mechanically or electrically due to selection. The cable 840 may be connected to the linear link 832 and the drive shaft 852 may be connected to the rotary link 831. However, the connection between the link 830 and the locking device 820 may vary. Referring to FIG. 19A, the locking device 820 is in an unlocked state, the brake 754 is spaced apart from the first shaft 751 or the second shaft 752, and the locking gas spring 723 is unlocked when pulled by pressure, thereby allowing the control panel 770 to be moved in a diagonal direction by enabling movement thereof on three axes for up and down, forward and backward, and left and right.

Referring to FIG. 19B, the locking device 820 is operated in a locked state, the brake 754 comes in contact with the first shaft 751 or the second shaft 752 to prevent rotation through friction, and the locking gas spring 723 is not pressed to prevent an up and down movement of the connecting unit 720 in a locked state, thereby controlling a movement of the control panel 770 so that the control panel 770 may be fixed at a particular position.

When comparing states illustrated in FIGS. 19A and 19B, FIG. 19B shows a state in which the control panel 770 is normally arranged to be fixed at a particular position.

When the user wishes to move the control panel 770, the user may unlock the locking device 820 to enable rotation about the first shaft 751 and the second shaft 752 and up and down movement of the connecting unit 720, thereby adjusting a position of the control panel 770.

In FIG. 19A, as the linear link 832 moves closer to the actuator 851, the locking device 820 is unlocked, and in detail, as the cable 840 is pressed closer to the actuator 851, the linear link 832 connected to the cable 840 may move along a straight line, as the rotary link 831 rotates counterclockwise about the drive shaft 852 on the linear link 832, the linear link 832 may be positioned adjacent to the first shaft 751 or the second shaft 752, and then the brake 754 connected to the linear link 832 may be loosened and then released.

Due to the linear movement of the linear link 832, the locking gas spring 723 that is connected to the linear link 832 and is normally in a locked state may be pulled and unlocked. In this way, the brake 754 and the locking gas spring 723 that restrict movement of the control panel 770.

When the locking device 820 is operated by the actuator 851, the drive shaft 852 connected to the actuator 851 may rotate counterclockwise to rotate the rotary link 831, and accordingly, the linear link 832 connected to the rotary link 831 may move along a straight line to unlock the brake 754 and the locking gas spring 723. Thus, the link 830 that moves first may vary depending on whether the locking device 820 is mechanically or electrically operated.

Referring to FIG. 19A, as the linear link 832 moves in one direction closer to the actuator 851, the rotary link 831 rotates counterclockwise and moves closer to the first shaft 751 or the second shaft 752 in a direction (the other direction) opposite to the one direction, and thus, from the perspective of linear motion, the linear link 832 and the rotary link 831 may move in opposite directions to each other.

Hereinafter, the one direction refers to a downward direction based on the drawing, and the other direction refers to an upward direction based on the drawing, which is the direction opposite to the one direction.

That is, the locking gas spring 723 connected to the linear link 832 and the brake 754 connected to the rotary link 831 may be unlocked by forces acting in opposite directions.

In FIG. 19B, the brake 754 is operated by receiving force in the one direction due to the rotating link 831 to prevent rotation of the first shaft 751 or the second shaft 752, and the locking gas spring 723 may be locked by receiving force in the other direction, thereby limiting vertical movement of the connecting unit 720.

When the locking unit 810 is changed from the state illustrated in FIG. 19B to the state illustrated in FIG. 19A, the brake 754 in FIG. 19A is released by receiving force in the other direction as the rotary link 831 rotates counterclockwise, and the locking gas spring 723 may be unlocked by receiving a force in the one direction.

In the ultrasonic imaging apparatus 700 according to the embodiment, because the locking unit 810 requires forces in different directions to simultaneously lock or unlock the brake 754 and the locking gas spring 723, and the required forces may partially cancel each other, the locking unit 810 may be operated with a smaller force than when it requires a force in the same direction to simultaneously lock or unlock the brake 754 and the locking gas spring 723, thereby reducing the size of the actuator 851 that provides power.

FIG. 20A is a cross-sectional view illustrating an operation of a locking unit 810 in an ultrasonic imaging apparatus 700 according to a 1st-2 embodiment, and FIG. 20B is a cross-sectional view illustrating an operation of the locking unit 810 in the ultrasonic imaging apparatus 700 according to the 1st-2 embodiment.

FIGS. 20A to 23B show locking units 810 according to other embodiments, which differ in a shape and an operation method of a locking device 820 and a link 830 compared to the locking unit 810 of FIGS. 19A and 19B, each of the locking units 810 including an actuator 851 connected to a drive shaft 852 while not directly exposed unlike in FIGS. 19A and 19B, and only differences from the embodiment of FIGS. 19A and 19B will be described.

In FIG. 20A, the linear link 832 is connected to the cable 840 in the one direction and to the first shaft 751 or the second shaft 752 in the other direction, and as the cable 840 provided in the one direction moves in the other direction, the linear link 832 becomes closer to the first shaft 751 or the second shaft 752, so that the brake 754 is loosened and the locking gas spring 723 is pulled in the other direction, and accordingly, the locking device 820 may be unlocked.

As the cable 840 is provided in the one direction, the brake 754 and the locking gas are simultaneously unlocked while moving in the other direction and simultaneously locked while moving in the one direction, and thus, they may be unlocked by a force in the same direction unlike in FIGS. 19A and 19B.

Because the brake 754 is connected to a side of the linear link 832 in the other direction and the cable 840 is connected to a side of the linear link 832 in the one direction, the brake 754 and the locking gas spring 723 may be unlocked only with linear movement of the linear link 832. Thus, when the locking device 820 is mechanically operated, the locking device 820 may be unlocked by the cable 840 connected to the side of the linear link 832 in the one direction regardless of movement of the rotary link 831.

When the locking device 820 is electrically operated, the locking device 820 may be unlocked by moving the linear link 832 while the rotary link 831 connected to the linear link 832 rotates due to the drive shaft 852 and the actuator 851, and as shown in FIG. 20A, as the rotary link 831 rotates counterclockwise, the linear link 832 moves along a straight line in the other direction to thereby unlock the brake 754 and the locking gas spring 723.

Referring to FIG. 20B showing a normal state in which the locking device 820 is operated, the linear link 832 pulls the brake 754 connected to the first shaft 751 or the second shaft 752 to control forward and backward and left and right movements of the control panel 770, and the locking gas spring 723 is not pulled in the other direction to prevent up and down movement of the connecting unit 720 in a locked state, thereby controlling the up and down movement of the control panel 770.

When the locking unit 810 is changed from the state illustrated in FIG. 20B to the state illustrated in FIG. 20A, when the locking device 820 is mechanically operated, the cable 840 and the linear link 832 move in the other direction to unlock the locking device 820, or when electrically operated, the rotary link 831 rotates counterclockwise due to the drive shaft 852 and the linear link 832 connected to the rotary link 831 moves along a straight line in the other direction to unlock the locking device 820, and as a result, the brake 754 and the locking gas spring 723 are unlocked, thereby allowing the control panel 770 to move freely.

FIG. 21A is a cross-sectional view illustrating an operation of a locking unit 810 in an ultrasonic imaging apparatus 700 according to a 1st-3 embodiment, and FIG. 21B is a cross-sectional view illustrating an operation of the locking unit 810 in the ultrasonic imaging apparatus 700 according to the 1st-3 embodiment.

Referring to FIGS. 21A and 21B, links 830 are provided as a multi-articulated link, and some of the links 830 are connected to a drive shaft 852 and may have linear or rotational movement due to rotation of the drive shaft 852.

The link 830 connected to the drive shaft 852 is a rotary link 831 which rotates together as the drive shaft 852 rotates and is connected to a linear link 832 to move the linear link 832.

Referring to FIG. 21B showing a normal state in which the locking device 820 is operated, the linear link 832 pulls a brake 754 connected to the first shaft 751 or the second shaft 752 to control forward and backward and left and right movements of the control panel 770, and a locking gas spring 723 connected to a cable 840 is not pulled in the one direction to prevent up and down movement of the connecting unit 720 in a locked state, thereby controlling the up and down movement of the control panel 770.

Referring to FIG. 21A showing a state in which the locking device 820 is unlocked, when the cable 840 or an actuator 851 is operated to cause the drive shaft 852 to rotate counterclockwise, the rotary link 831 connected to the drive shaft 852 rotates together to move the linear link 832 in the other direction to be adjacent to the first shaft 751 or the second shaft 752 and accordingly release the brake 754, and as the cable 840 moves in the one direction, the locking gas spring 723 may be pulled in the one direction and then unlocked.

When the locking unit 810 is changed from the state illustrated in FIG. 21B to the state illustrated in FIG. 21A, as the drive shaft 852 rotates counterclockwise due to a movement of the cable 840 or an operation of the actuator 851, the rotary link 831 also rotates counterclockwise so that the linear link 832 becomes adjacent to the first shaft 751 or the second shaft 752. In this case, rotation of the first shaft 751 or the second shaft 752 is allowed by loosening of the brake 754 that controls the rotation through friction around a circumference of the first shaft 751 or the second shaft 752, while the locking gas spring 723 connected to the cable 840 is unlocked by being pressed or pulled in the one direction, and thus, an up and down movement of the connecting unit 720 and the control panel 770 is allowed.

Similar to the embodiment of FIG. 19A, in the embodiment of FIG. 21A, because the cable 840 moves in the one direction to unlock the locking gas spring 723 while the linear link 832 moves in the other direction to be closer to the first shaft 751 or the second shaft 752 to release the brake 754, the locking gas spring 723 and the brake 754 may be unlocked by forces in opposite directions.

Therefore, because forces in different directions are required to simultaneously lock or unlock the brake 754 and locking gas spring 723, the required forces may partially cancel each other, enabling operation with a relatively small force and reducing the size of the actuator 851 that provides power. FIG. 22A is a cross-sectional view illustrating an operation of a locking unit 810 in an ultrasonic imaging apparatus 700 according to a 1st-4 embodiment, and FIG. 22B is a cross-sectional view illustrating an operation of the locking unit 810 in the ultrasonic imaging apparatus 700 according to the 1st-4 embodiment.

The embodiment of FIGS. 22A and 22B is similar to the embodiment of FIGS. 21A and 21B in that links 830 are provided as a multi-articulated link, but is different therefrom in a shape of a brake 754.

Referring to FIGS. 22A and 22B, the brake 754 is provided around the first shaft 751 or the second shaft 752 in the form of tongs but not in the form of a band, so that the brake 754 is released when the tongs are spread to both sides and is operated when the tongs are brought inward.

Referring to FIG. 22B showing a normal state in which the locking device 820 is operated, when the linear link 832 presses the brake 754 connected to the first shaft 751 or the second shaft 752 in the other direction, the brake 754 is brought inward to be operated, and a locking gas spring 723 connected to a cable 840 is not pulled in the one direction to prevent up and down movement of the connecting unit 720 in a locked state, thereby controlling up and movement of the control panel 770.

Referring to FIG. 22A showing a state in which the locking device 820 is unlocked, when the cable 840 or an actuator 851 is operated to cause the drive shaft 852 to rotate counterclockwise, the rotary link 831 connected to the drive shaft 852 rotates together to move the linear link 832 adjacent to the drive shaft 852 and spread the brake 754 to either side to release the brake 754, and as the cable 840 moves in the one direction, the locking gas spring 723 may be pulled in the one direction and then unlocked.

When the locking unit 810 is changed from the state illustrated in FIG. 22B to the state illustrated in FIG. 22A, as the drive shaft 852 rotates counterclockwise due to movement of the cable 840 or operation of the actuator 851, the rotary link 831 also rotates counterclockwise so that the linear link 832 moves toward the drive shaft 852 and accordingly is spaced apart from the first shaft 751 or the second shaft 752. In this case, rotation of the first shaft 751 or the second shaft 752 is allowed by loosening the brake 754 which controls rotation through friction around a circumference of the first shaft 751 or the second shaft 752, while the locking gas spring 723 connected to the cable 840 is unlocked by being pressed or pulled in the one direction, and thus, an up and down movement of the connecting unit 720 and the control panel 770 is allowed.

FIG. 23A is a cross-sectional view illustrating an operation of a locking unit 810 in an ultrasonic imaging apparatus 700 according to a 1st-5 embodiment, and FIG. 23B is a cross-sectional view illustrating an operation of the locking unit 810 in the ultrasonic imaging apparatus 700 according to the 1st-5 embodiment.

The embodiment of FIGS. 23A and 23B is similar to the embodiment of FIGS. 21A and 21B in that links 830 are provided as a multi-articulated link, but is different therefrom in a shape of a brake 754.

Referring to FIGS. 23A and 23B, the brake 754 is not provided in the form of a band around the first shaft 751 or the second shaft 752, but is provided on one side of the first shaft 715 or the second shaft 752 in a form that allows control of rotation via a frictional force generated by a contact with the one side of the first shaft 751 or the second shaft 752, and the brake 754 is operated when it comes in contact with the first shaft 751 or the second shaft 752 and is released when it is spaced apart therefrom.

Referring to FIG. 23B showing a normal state in which the locking device 820 is operated, when the linear link 832 presses the brake 754 connected to the first shaft 751 or the second shaft 752 in the other direction, the brake 754 is operated by contacting the first shaft 751 or the second shaft 752, and a locking gas spring 723 connected to the cable 840 is not pulled in the one direction to prevent up and down movement of the connecting unit 720 in a locked state, thereby controlling up and movement of the control panel 770. Referring to FIG. 23A showing a state in which the locking device 820 is unlocked, when the cable 840 or an actuator 851 is operated to cause the drive shaft 852 to rotate counterclockwise, the rotary link 831 connected to the drive shaft 852 rotates together to move the linear link 832 adjacent to the drive shaft 852 and space the brake 754 apart from the first shaft 751 or the second shaft 752 to release the brake 754, and as the cable 840 moves in the one direction, the locking gas spring 723 may be pulled in the one direction and then unlocked.

When the locking unit 810 is changed from the state illustrated in FIG. 23B to the state illustrated in FIG. 23A, as the drive shaft 852 rotates counterclockwise due to movement of the cable 840 or operation of the actuator 851, the rotary link 831 also rotates counterclockwise so that the linear link 832 moves toward the drive shaft 852 and is accordingly spaced apart from the first shaft 751 or the second shaft 752 to allow rotation of the first shaft 751 or the second shaft 752 by spacing away the brake 754 provided on one side of the first shaft 751 or the second shaft 752, and the locking gas spring 723 connected to the cable 840 is unlocked by being pressed or pulled in the one direction, thereby enabling up and down movement of the connecting unit 720 and the control panel 770.

FIG. 24A is a close-up perspective view of the ultrasonic imaging apparatus 700 according to the second embodiment, and FIG. 24B is a close-up perspective view of the ultrasonic imaging apparatus 700 according to the second embodiment.

The ultrasonic imaging apparatus 700 according to the second embodiment may include the single second shaft 752 provided in the second connection frame 742, the first rotating member 781 connected to the second shaft 752, and the second rotating member 782 not directly connected to the second shaft 752.

The second shaft 752 connected to the first rotating member 781 and provided in the second connection frame 742 may control the rotation of the second connection frame 742, and the axis provided in the second rotating member 782 is not connected to the second connection frame 742 and is therefore unrelated to the rotation of the second connection frame 742. Referring to FIGS. 24A and 24B, because the first rotating member 781 and the second rotating member 782 are respectively connected to the second arms 722, the second shaft 752 may determine the rotation of the second connection frame 742 with respect to the second arm 722, and the first arms 721, which are not shown, may be respectively connected to a pair of first shafts 751.

FIG. 25A is a cross-sectional view illustrating an operation of a locking unit 810 in an ultrasonic imaging apparatus according 700 to a 2nd-1 embodiment, FIG. 25B is a cross-sectional view illustrating an operation of the locking unit 810 in the ultrasonic imaging apparatus 700 according to the 2nd-1 embodiment, and FIG. 26 is a close-up perspective view of a second connection frame 742 provided on a bottom of a control panel 770 in the ultrasonic imaging apparatus according 700 to the 2nd-1 embodiment. Referring to FIG. 25A, a brake 754 is provided around a circumference of the second shaft 752 in the form of a band that controls rotation via a frictional force generated due to contact with the circumference of the second shaft 752, and is operated when it comes in contact with the circumference of the second shaft 752 and is released when it is spaced apart from or loosely located away from the second shaft 752.

Referring to FIG. 25B showing a normal state in which the locking device 820 is operated, when a linear link 832 presses a brake 754 connected to the second shaft 752 in the one direction, the brake 754 is operated by converging inward, and a locking gas spring 723 connected to a cable 840 is not pulled in the one direction to prevent up and down movement of the connecting unit 720 in a locked state, thereby controlling up and movement of the control panel 770.

Referring to FIG. 25A showing a state in which the locking device 820 is unlocked, when the cable 840 is operated to move the linear link 832 in the one direction or an actuator 851 is operated to cause a rotary link 831 to rotate counterclockwise, the rotary link 831 connected to the brake 754 moves adjacent to the second shaft 752 to loosen the brake 754 provided around the second shaft 752, and as the cable 840 moves in the one direction, the locking gas spring 723 may be pulled in the one direction and then unlocked.

When the locking unit 810 is changed from the state illustrated in FIG. 25B to the state illustrated in FIG. 25A, as the rotary link 831 rotates counterclockwise due to movement of the cable 840 or operation of the actuator 851, the linear link 832 is brought into proximity to the second shaft 752 to loosen the brake 754 which controls rotation via friction around the second shaft 752, thereby allowing rotation of the second shaft 752, while the locking gas spring 723 connected to the cable 840 is unlocked by being pressed or pulled in the one direction, thereby enabling up and down movement of the connecting unit 720 and the control panel 770.

Similar to the embodiment of FIG. 19A, in the embodiment of FIG. 25A, because the cable 840 moves in the one direction to unlock the locking gas spring 723 while the linear link 832 moves in the other direction to be closer to the second shaft 752 to release the brake 754, the locking gas spring 723 and the brake 754 may be unlocked by forces in opposite directions.

FIG. 26 is a close-up perspective view of the second connection frame 742 provided on the bottom of the control panel 770, and the single second shaft 752 and the actuator 851 are provided in the second connection frame 742, to control rotation of the second connection frame 742 only via control of the second shaft 752.

Because the cable 840 is connected to the linear link 832, the linear link 832 is connected to the rotary link 831, and the rotary link 831 is connected to the brake 754, the brake 754 may be controlled by movement of the cable 840 or movement of the drive shaft 852 connected to the rotary link 831, and the locking gas spring 723 is connected to the cable 840 so that it may be operated by movement of the linear link 832 due to an operation of the cable 840 or rotation of the drive shaft 852.

Although FIGS. 19A to 23B show that the cable 840 is a single cable, because the connecting unit 720 includes the first arm 721 and the second arm 722 in which the locking gas springs 723 are respectively provided, the two locking gas springs 723 may be respectively connected to a pair of cables 840, or in some cases, the single cable 840 may be connected to the two locking gas springs 723.

In addition, for the first arm 721 and the second arm 722 that are not provided with the locking gas spring 723, a normal gas spring may be provided to compensate for weight.

FIG. 27 is a close-up perspective view of first arrangement of a gas spring cable 841 in the ultrasonic imaging apparatus 70, according to an embodiment, FIG. 28 is a close-up perspective view of the first arrangement of the gas spring cable 841 in the ultrasonic imaging apparatus 700, according to the embodiment, FIG. 29 is a close-up perspective view of second arrangement of the gas spring cable 841 in the ultrasonic imaging apparatus 700, according to an embodiment, and FIG. 30 is a close-up perspective view of the second arrangement of the gas spring cable 841 in the ultrasonic imaging apparatus 700, according to the embodiment.

The locking gas spring 723 is provided in the first arm 721 or the second arm 722 to control movement in a locked state in normal times, and may be unlocked when pressed or pulled in the one direction to enable up and down movement of the first arm 721 or the second arm 722.

The gas spring cable 841 has one end connected to the locking gas spring 723 and another end connected to the link 830 provided in the locking unit 810, and may extend from the first arm 721 where the locking gas spring 723 is provided to the first connection frame 741 where the link 830 is provided, or from the second arm 722 to the second connection frame 742 where the link 830 is provided.

The gas spring cable 841 serves to connect the locking gas spring 723 to the link 830, and when the link 830 moves or rotates due to the operation of the locking device 820, the gas spring cable 841 moves with the link 830 to operate the locking gas spring 723. FIGS. 27 and 28 are diagrams illustrating the first arrangement of the gas spring cable 841, and the gas spring cable 841 may extend from the first arm 721 to the second connection frame 742 in order to simultaneously control the locking gas springs 723 provided in the first arm 721 and the second arm 722.

Referring to FIG. 27, the gas spring cable 841 is provided to pass through the first lifting arm 731 including the first arm 721 and the second arm 722, and thus, the gas spring cable 841 may pass through or be located adjacent to the third shaft 753 which is a rotation axis of the first arm 721 and the second arm 722.

The gas spring cable 841 may simultaneously control the operation of the locking gas springs 723 provided in the first arm 721 and the second arm 722 through pressure from the second connection frame 742. Although FIG. 27 shows that the gas spring cable 841 is provided only in the first lifting arm 731, the gas spring cable 841 may also be provided in the second lifting arm 732, and the operation of the gas spring cables 841 may be controlled simultaneously in the second connection frame 742.

In the first arrangement of the gas spring cable 841, because the gas spring cable 841 is mechanically operated in the second connection frame 742, the gas spring cable 841, which is a mechanical cable, may be provided on the third shaft 753 that is the rotation axis of the first arm 721 and the second arm 722.

The radius of curvature of the gas spring cable 841 may be 100 mm or more. For example, the radius of curvature of the gas spring cable 841 may be about 100 mm to about 200 mm.

In the first arrangement, the gas spring cable 841 is exposed to the outside of the first arm 721 and the second arm 722 at a position where the third shaft 753 is provided, so as not to hinder the rotation of the third shaft 753, which may increase the overall volume and create an unfavorable impression in appearance.

When the first arm 721 and the second arm 722 are moved to move the control panel 770 as shown in FIG. 28, problems occur in that a portion of the gas spring cable 841 provided adjacent to the third shaft 753 may become kinked, causing damage or reducing its lifespan, resistance may occur when moving the first arm 721 and the second arm 722 due to physical characteristics of the gas spring cable 841, which is a mechanical cable, and the control panel 770 may only be moved within a length of the gas spring cable 841.

FIGS. 29 and 30 are diagrams illustrating second arrangement of the gas spring cable 841, and when compared to the first arrangement, a length of the gas spring cable 841A may vary, and a position at which the gas spring cable 841A is provided in the connection 720 may be limited.

Referring to FIG. 29, a plurality of gas spring cables 841A may be arranged, some of which are provided on the first shaft 751 and the first arm 721 while the others are provided on the second shaft 752 and the second arm 722, so that the plurality of gas spring cables 841A may be spaced apart from each other.

On the left side of the third shaft 753, a gas spring cable 841A connected to the locking gas spring 723 provided in the second arm 722 is located, and on the right side, a gas spring cable 841A connected to the locking gas spring 723 provided in the first arm 721 may be located.

The radius of curvature of the gas spring cable 841A may be 100 mm or more. For example, the radius of curvature of the gas spring cable 841A may be about 100 mm to about 200 mm.

In the second arrangement of the gas spring cable 841A, in which one gas spring cable 841A is provided adjacent to the first connection frame 741 and one gas spring cable is provided adjacent to the second connection frame 742, the gas spring cable 841 may not pass through the first lifting arm 731 or the second lifting arm 732 and thus may not be provided adjacent to the third shaft 753, so problems in the first arrangement of the gas spring cable 841 may be solved.

Referring to FIG. 30, even though the control panel 770 is moved in a 3D space, restrictions due to the gas spring cables 841A may not occur, and each of the gas spring cables 841 may operate simultaneously via electrical signals. The gas spring cable 841A may be configured to operate by electrical signals. For example, each of the gas spring cable 841A disposed adjacent to the first connection frame 741 and the gas spring cable 841A disposed adjacent to the second connection frame 742 may be operated by separate actuators (or motors). The separate actuators may be connected to the electric button by wires. Because the wire has a different structure and material from the gas spring cable 841A, it can bend better than the gas spring cable 841A. The radius of curvature of the wire may be smaller than the radius of curvature of the gas spring cable 841A. The radius of curvature of the wire may be less than 100 mm. The radius of curvature of the wire is greater than 0 and may be 90 mm or less.

In the first arrangement of the gas spring cable 841 illustrated in FIGS. 27 and 28, because the gas spring cable 841 is mechanically operated, the gas spring cable 841 is provided to pass through the first arm 721 and the second arm 722 and allows the locking gas springs 723 provided in the first arm 721 and the second arm 722 to be operated via pulling or pressing in the second connection frame 742.

In FIGS. 27 and 28, the gas spring cable 841 is provided as a mechanical cable that may have resistance to movement of the first arm 721 and the second arm 722, and thus, allows the control panel 770 to move only within the length of the gas spring cable 841. On the other hand, in the second arrangement of the gas spring cable 841 illustrated in FIGS. 29 and 30, because the gas spring cables 841 are electrically operated, the gas spring cables 841 are not provided adjacent to the third shaft 753 but are respectively arranged adjacent to the first connection frame 741 and the second connection frame 742, and only a thin electrical wire that electrically operates the gas spring cables 841 is provided adjacent to the third shaft 753, thereby solving the problems of resistance and limited radius of movement caused by the gas spring cable 841.

In the second arrangement, the gas spring cables 841 may be electrically operated to independently operate the locking gas springs 723 respectively provided in the first arm 721 and the second arm 722, thereby allowing the connecting unit 720 that is multi-articulated to be operated in more diverse forms.

Embodiments have been particularly shown and described with reference to the accompanying drawings.

It will be understood by those of ordinary skill in the art that various changes in form and details may be made therein without departing from technical idea or essential features of the disclosure.

The embodiments and all aspects thereof are merely examples and are not to be construed as limiting.

An ultrasonic imaging apparatus according to the disclosure may improve a movement radius and movement of a control panel.

The effects of the disclosure are not limited to those described above, and effects not described will be apparent to one of ordinary skill in the art from this specification and the accompanying drawings.

What is claimed is:

1. An ultrasonic imaging apparatus comprising:

a main body;

a connecting unit configured to rotate and move with respect to the main body; and a control panel provided on an end of the connecting unit to be movable up, down, right, left, or diagonally while remaining horizontal with respect to the main body, wherein the connecting unit comprises a first lifting arm and a second lifting arm spaced apart from each other, wherein the main body comprises a first connection frame provided to be connected to an end of the connecting unit so that the connecting unit rotates with respect to a first shaft, the control panel comprises a second connection frame provided to be connected to another end of the connecting unit so that the connecting unit rotates with respect to a second shaft, wherein each of the first lifting arm and the second lifting arm comprises:

a first arm provided with four link bars forming a parallelogram in a same plane and configured to rotate and move with respect to the main body;

a second arm provided with four link bars forming a parallelogram in a plane provided independently of the first arm and configured to rotate and move with respect to the first arm; and a third shaft provided between the first arm and the second arm so that the first arm and the second arm rotate relative to each other, wherein each of the first lifting arm and the second lifting arm is configured to rotate about the first shaft with respect to the first connection frame provided on the main body at one end, and is connected to the second connection frame provided on a bottom of the control panel at another end.

2. The ultrasonic imaging apparatus of claim 1, wherein the four link bars forming the parallelogram comprise:

two horizontal bars arranged parallel to each other; and two vertical bars each being provided at two ends of the two horizontal bars, and the horizontal bars are configured to rotate about arm shafts provided on the vertical bars.

3. The ultrasonic imaging apparatus of claim 2, wherein the connecting unit comprises a locking gas spring that is provided between the horizontal bars to compensate for weight during an up and down movement and to fix up and down positions, and the locking gas spring is provided in at least one of the first lifting arm or the second lifting arm.

4. The ultrasonic imaging apparatus of claim 3, wherein the first connection frame comprises a brake configured to prevent rotation of the first arm configured to rotate about the first shaft, and the second connection frame comprises a brake configured to prevent rotation of the second arm configured to rotate about the second shaft.

5. The ultrasonic imaging apparatus of claim 4, wherein the connecting unit further comprises a brake wire connected to the locking gas spring and the brake to determine whether the control panel is to be moved.

6. The ultrasonic imaging apparatus of claim 5, wherein the first shaft, the second shaft, and the third shaft are arranged parallel to one another and remain parallel even when an operation of the brake wire connected to the brake is released and thus the control panel is moved.

7. The ultrasonic imaging apparatus of claim 6, wherein the ultrasonic imaging apparatus further comprises an actuator connected to the brake wire and configured to determine whether to operate the brake.

8. The ultrasonic imaging apparatus of claim 6, wherein the arm shafts are provided as two arm shafts on each of the vertical bars and located to be offset from each other so that the first arm and the second arm each form a parallelogram in a same plane.

9. The ultrasonic imaging apparatus of claim 6, wherein the control panel is further configured to rotate about the second shaft with the second connection frame provided on the bottom to perform a plane movement, and the second arm of any one of the first lifting arm and the second lifting arm comprises a first rotating member connected to the second shaft, and the second arm of the other one of the first lifting arm and the second lifting arm comprises a second rotating member not connected to the second shaft, and connected to the first rotating member obliquely with respect to the second shaft so as to move with the first rotating member.

10. The ultrasonic imaging apparatus of claim 9, wherein the first rotating member has a cross-sectional area greater than a cross-sectional area of the second rotating member, and the second rotating member is configured to support a bottom of the first rotating member.

11. The ultrasonic imaging apparatus of claim 4, wherein the third shaft is provided as a plurality of third shafts each being connected to the vertical bar of the first arm and the vertical bar of the second arm so that the first arm and the second arm each rotate about the third shaft.

12. The ultrasonic imaging apparatus of claim 11, wherein the connecting unit further comprises a brake configured to prevent the rotation of the first arm or the second arm.

13. The ultrasonic imaging apparatus of claim 4, wherein the locking gas spring is provided in the first lifting arm or the second lifting arm so that up and down positions are fixed by one of the first lifting arm and the second lifting arm, and the first lifting arm and the second lifting arm are arranged asymmetrically to each other due to different lengths of the horizontal bar so that positions of the third shafts in the first lifting arm and the second lifting arm are different from each other.

14. An ultrasonic imaging apparatus comprising:

a main body;

a connecting unit configured to rotate and move with respect to the main body;

a control panel provided on an end of the connecting unit and configured to be movable up, down, right, left, or diagonally while remaining horizontal with respect to the main body; and a locking unit configured to control a movement of the control panel, wherein the locking unit comprises:

a locking gas spring configured to control an up and down movement of the control panel;

a brake configured to control forward and backward and left and right movements of the control panel;

a locking device that is mechanically or electrically operated; and a link connected to the locking gas spring and the brake and moved by the locking device, wherein the locking unit is configured to simultaneously operate the locking gas spring and the brake, and wherein the locking gas spring and the brake receive forces in opposite directions to fix a position of the control panel.

15. The ultrasonic imaging apparatus of claim 14, wherein the link comprises:

a rotary link configured to rotate about one axis in response to an operation of the locking device; and a linear link configured to move along a straight line in response to the operation of the locking device, the rotary link and the linear link are connected to each other in a partially overlapping manner, so that an operation of one of the rotary link and the linear link causes an operation of the other link, and at least one of the rotary link or the linear link is connected to the locking device and is operated simultaneously by the operation of the locking device.

16. The ultrasonic imaging apparatus of claim 15, wherein the locking device comprises:

an actuator configured to move the link when electrically operated; and a drive shaft corresponding to the one axis of the link.

17. The ultrasonic imaging apparatus of claim 15, further comprising a gas spring cable configured to move the locking gas spring, wherein the gas spring cable has one end connected to the locking gas spring and another end connected to the link to operate the locking gas spring due to the operation of the locking device.

* * * * *